(12) United States Patent
Heinrich et al.

(10) Patent No.: US 10,575,849 B2
(45) Date of Patent: *Mar. 3, 2020

(54) SURGICAL INSTRUMENTS INCLUDING MEMS DEVICES

(71) Applicant: Covidien LP, Mansfield, MA (US)

(72) Inventors: Russell Heinrich, Madison, CT (US); Douglas Cuny, Bethel, CT (US)

(73) Assignee: COVIDIEN LP, Mansfield, MA (US)

( * ) Notice: Subject to any disclaimer, the term of this patent is extended or adjusted under 35 U.S.C. 154(b) by 111 days.

This patent is subject to a terminal disclaimer.

(21) Appl. No.: 15/946,763

(22) Filed: Apr. 6, 2018

(65) Prior Publication Data
US 2018/0221024 A1 Aug. 9, 2018

Related U.S. Application Data

(63) Continuation of application No. 15/156,417, filed on May 17, 2016, now Pat. No. 9,962,159, which is a (Continued)

(51) Int. Cl.
*A61B 17/068* (2006.01)
*A61B 17/072* (2006.01)
(Continued)

(52) U.S. Cl.
CPC ........ *A61B 17/072* (2013.01); *A61B 17/0469* (2013.01); *A61B 17/062* (2013.01); (Continued)

(58) Field of Classification Search
CPC ... A61B 17/068; A61B 17/072; A61B 17/062; A61B 18/1445; A61B 2019/464;
(Continued)

(56) References Cited

U.S. PATENT DOCUMENTS 4,508,253 A 4/1985 Green
5,395,033 A 3/1995 Byrne et al.
(Continued)

FOREIGN PATENT DOCUMENTS

EP 0647431 A2 4/1995
EP 0738501 A1 10/1996
(Continued)

OTHER PUBLICATIONS

Judy, Jack. Microelectromechanical systems (MEMS): fabrication, design and applications. 2001. Smart Mater. Struct. pp. 1115-1134.
(Continued)

*Primary Examiner* — Katherine M Rodjom
(74) *Attorney, Agent, or Firm* — Carter, DeLuca & Farrell, LLP

(57) ABSTRACT

Surgical instruments are disclosed that are couplable to or have an end effector or a disposable loading unit with an end effector, and at least one micro-electromechanical system (MEMS) device operatively connected to the surgical instrument for at least one of sensing a condition, measuring a parameter and controlling the condition and/or parameter.

10 Claims, 12 Drawing Sheets

Related U.S. Application Data continuation of application No. 14/884,393, filed on Oct. 15, 2015, now abandoned, which is a continuation of application No. 14/338,383, filed on Jul. 23, 2014, now Pat. No. 9,295,468, which is a continuation of application No. 13/030,434, filed on Feb. 18, 2011, now Pat. No. 8,808,311, which is a continuation of application No. 10/510,940, filed as application No. PCT/US03/13056 on Apr. 25, 2003, now abandoned.

(60) Provisional application No. 60/375,496, filed on Apr. 25, 2002, provisional application No. 60/375,495, filed on Apr. 25, 2002.

(51) Int. Cl.

| | | |
|---|---|---|
| *A61B 90/00* | (2016.01) | |
| *A61B 17/04* | (2006.01) | |
| *A61B 17/062* | (2006.01) | |
| *A61B 17/128* | (2006.01) | |
| *A61B 18/14* | (2006.01) | |
| *A61B 34/30* | (2016.01) | |
| *A61B 17/00* | (2006.01) | |
| *A61B 17/06* | (2006.01) | |
| *A61B 18/00* | (2006.01) | |

(52) U.S. Cl.
CPC .... *A61B 17/0686* (2013.01); *A61B 17/07207* (2013.01); *A61B 17/128* (2013.01); *A61B 18/1445* (2013.01); *A61B 34/30* (2016.02); *A61B 90/06* (2016.02); *A61B 2017/00022* (2013.01); *A61B 2017/0023* (2013.01); *A61B 2017/00066* (2013.01); *A61B 2017/0609* (2013.01); *A61B 2017/07214* (2013.01); *A61B 2017/07228* (2013.01); *A61B 2017/07257* (2013.01); *A61B 2017/07271* (2013.01); *A61B 2018/00648* (2013.01); *A61B 2018/00702* (2013.01); *A61B 2034/303* (2016.02); *A61B 2034/305* (2016.02); *A61B 2090/061* (2016.02); *A61B 2090/064* (2016.02)

(58) Field of Classification Search
CPC ........ A61B 2019/465; A61B 2019/467; A61B 2017/00022; A61B 2017/0003; A61B 2018/00648; A61B 34/30; A61B 2034/305; A61B 2090/064; A61B 2090/061

See application file for complete search history.

(56) References Cited

U.S. PATENT DOCUMENTS

| | | | |
|---|---|---|---|
| 5,518,163 A | 5/1996 | Hooven | |
| 5,562,239 A | 10/1996 | Boiarski et al. | |
| 5,667,517 A * | 9/1997 | Hooven | A61B 17/072 227/175.1 |
| 5,722,989 A | 3/1998 | Fitch et al. | |
| 5,807,261 A | 9/1998 | Benaron et al. | |
| 5,865,361 A | 2/1999 | Milliman et al. | |
| 5,911,353 A | 6/1999 | Bolanos et al. | |
| 5,915,616 A | 6/1999 | Viola et al. | |
| 5,964,394 A | 10/1999 | Robertson | |
| 5,976,156 A | 11/1999 | Taylor et al. | |
| 6,032,849 A | 3/2000 | Mastri et al. | |
| 6,045,560 A | 4/2000 | McKean et al. | |
| 6,092,422 A | 7/2000 | Binnig et al. | |
| 6,102,850 A * | 8/2000 | Wang | B25J 9/1689 414/2 |
| 6,127,811 A | 10/2000 | Shenoy et al. | |
| 6,221,023 B1 | 4/2001 | Matsuba et al. | |
| 6,231,565 B1 | 5/2001 | Tovey et al. | |
| 6,241,139 B1 | 6/2001 | Milliman et al. | |
| 6,288,534 B1 | 9/2001 | Starkweather et al. | |
| 6,330,965 B1 | 12/2001 | Milliman et al. | |
| 6,716,233 B1 | 4/2004 | Whitman | |
| 6,972,199 B2 | 12/2005 | Lebouitz et al. | |
| 7,223,279 B2 | 5/2007 | Burbank et al. | |
| 7,229,465 B2 | 6/2007 | Burbank et al. | |
| 7,618,376 B2 | 11/2009 | Kimball | |
| 8,118,206 B2 | 2/2012 | Zand et al. | |
| 8,808,311 B2 | 8/2014 | Heinrich et al. | |
| 9,295,468 B2 | 3/2016 | Heinrich et al. | |
| 9,561,031 B2 | 2/2017 | Heinrich et al. | |
| 9,962,159 B2 | 5/2018 | Heinrich et al. | |
| 2001/0020166 A1 | 9/2001 | Daly et al. | |
| 2002/0077568 A1 | 6/2002 | Haddock | |
| 2002/0107658 A1 | 8/2002 | McCall et al. | |
| 2003/0105478 A1 | 6/2003 | Whitman et al. | |
| 2003/0120306 A1 | 6/2003 | Burbank et al. | |
| 2004/0236352 A1 | 11/2004 | Wang et al. | |
| 2004/0267310 A1 | 12/2004 | Racenet et al. | |
| 2005/0131390 A1 | 6/2005 | Heinrich et al. | |
| 2012/0016362 A1 | 1/2012 | Heinrich et al. | |
| 2014/0135604 A1 | 5/2014 | Cuesta Valentin et al. | |
| 2014/0336641 A1 | 11/2014 | Heinrich et al. | |
| 2016/0030042 A1 | 2/2016 | Heinrich et al. | |
| 2016/0256164 A1 | 9/2016 | Heinrich et al. | |

FOREIGN PATENT DOCUMENTS

| | | |
|---|---|---|
| EP | 0537570 B1 | 1/1998 |
| WO | 9952489 A1 | 10/1999 |
| WO | 0051486 A1 | 9/2000 |
| WO | 0162164 A2 | 8/2001 |
| WO | 03020139 A2 | 3/2003 |
| WO | 03090630 A2 | 11/2003 |

OTHER PUBLICATIONS

Goosen, J. F L; French, P.J.; Sarro, P.M., "Pressure, flow and oxygen saturation sensors on one chip for use in catheters," MEMS 2000. Proceedings of the Thirteenth Annual International Conference on Micro Electro Mechanical Systems. pp. 537,540,Jan. 23-27, 2000.
P. Detemple, "Microtechnology in Modern Health Care", Medical Device Technology, pp. 18-25, (1998).

* cited by examiner

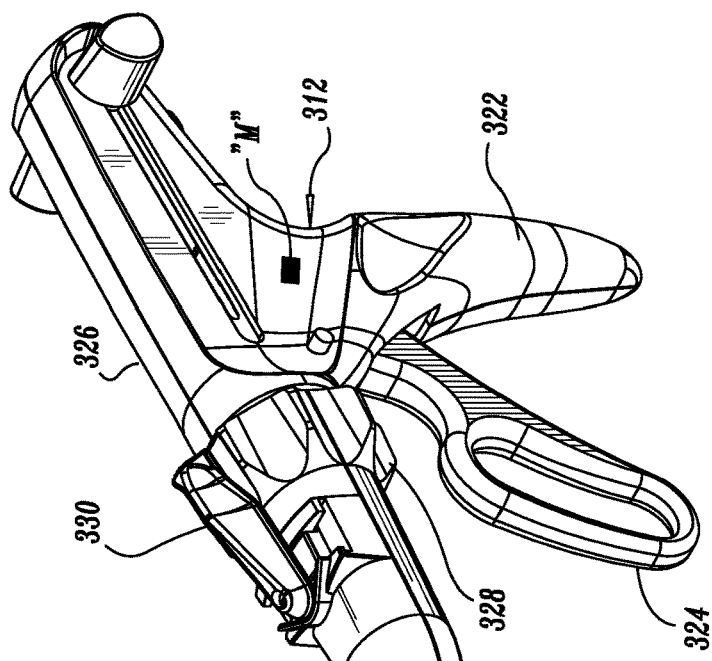
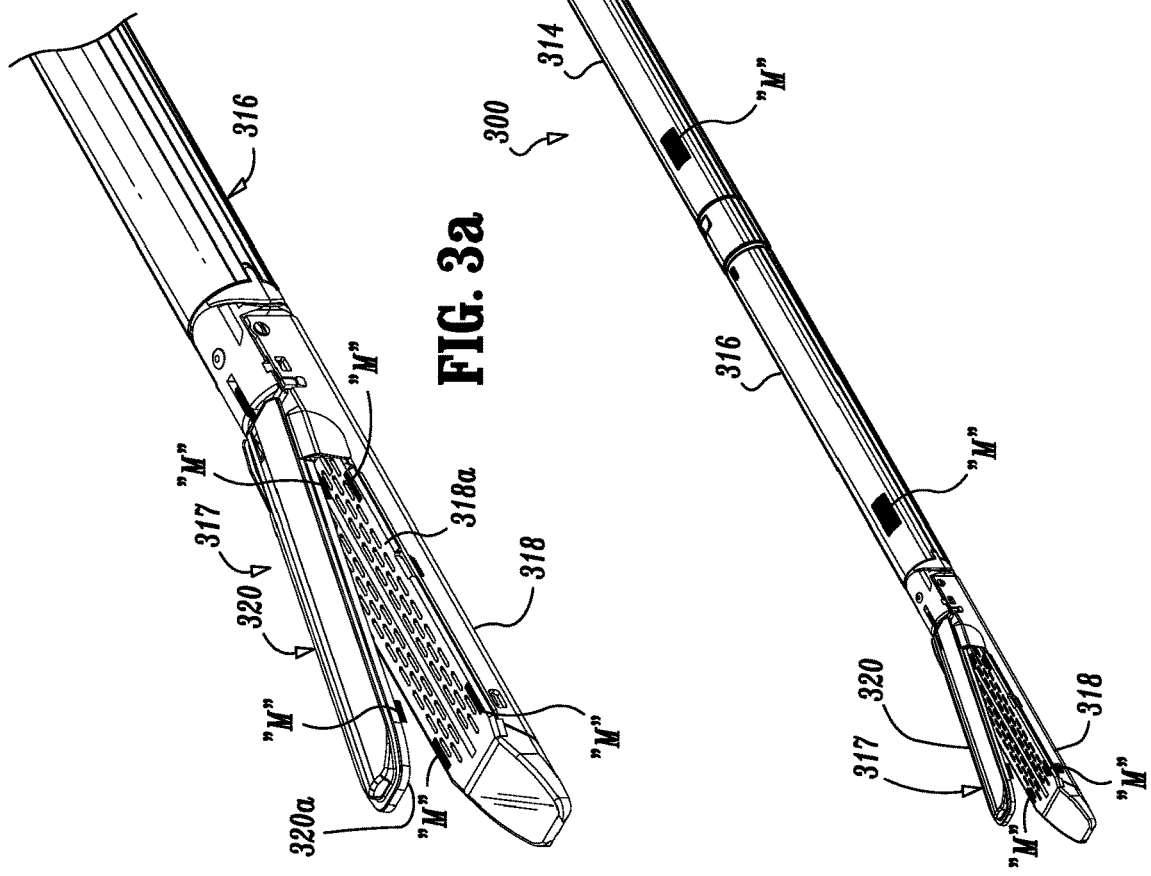

SURGICAL INSTRUMENTS INCLUDING MEMS DEVICES

CROSS-REFERENCE TO RELATED APPLICATIONS

The present application is a continuation application of U.S. patent application Ser. No. 15/156,417, filed May 17, 2016, which is a continuation application of U.S. patent application Ser. No. 14/884,393, filed on Oct. 15, 2015, which is a continuation application of U.S. patent application Ser. No. 14/338,383, filed on Jul. 23, 2014, (now U.S. Pat. No. 9,295,468) which is a continuation application of U.S. patent application Ser. No. 13/030,434, filed on Feb. 18, 2011 (now U.S. Pat. No. 8,808,311), which is a continuation application of U.S. patent application Ser. No. 10/510,940, filed on Oct. 8, 2004 (now Abandoned), which is a national stage entry of International Patent Application No. PCT/US03/13056, filed on Apr. 25, 2003, which claims the benefit of and priority to U.S. Provisional Application Ser. No. 60/375,495 and U.S. Provisional Application Ser. No. 60/375,496, both of which were filed on Apr. 25, 2002, and the entire disclosures of each of which are incorporated herein by reference.

BACKGROUND

1. Technical Field

The present disclosure relates to surgical instruments and, more particularly to mechanical, electro-mechanical and energy based surgical instruments and systems.

The present disclosure relates generally to surgical instruments and systems and, more specifically, to surgical stapler instruments and systems and energy based instruments and systems, having micro-electromechanical system (MEMS) devices for sensing, monitoring, controlling, measuring and/or regulating conditions and/or parameters associated with the performance of various surgical procedures.

2. Background of Related Art

Surgical instruments used in open and minimally invasive surgery are limited in their ability to sense and/or control conditions and/or parameters and factors critical to effective operation. For example, conventional surgical instruments cannot measurably detect the amount of tissue positioned between tissue contacting surfaces of an end effector of the surgical instrument.

Micro-electromechanical systems (MEMS) are integrated micro devices or systems combining electrical and mechanical components. They are fabricated using integrated circuitry (i.e., I.C.) batch processing techniques and can range in size from micrometers to millimeters. These micro-electromechanical systems sense, control and/or actuate on the micro scale, and function individually or in arrays to generate effects on the macro scale.

In general, MEMS devices are complex systems which individually include one or more electrical systems and/or one or more micro-mechanical systems. The micro-mechanical systems are fabricated using many of the same fabrication techniques that have miniaturized electronic circuits and made mass production of silicon integrated circuit chips possible. In particular, MEMS devices include mechanical micro-structures, micro-sensors, micro-actuators and electronics integrated in the same environment (i.e., on a silicon chip) by using micro-fabrication technology. Micro-fabrication technology enables fabrication of large arrays of devices, which individually perform simple tasks but in combination can accomplish complicated functions.

MEMS devices are advantageous for many reasons. In particular, MEMS devices can be so small that hundreds can be fit in the same space, which perform the same or many different functions, as compared to a single macro-device, which performs a single function. Moreover, using I.C. batch processing techniques, hundreds to thousands of these MEMS devices can be fabricated on a single silicon wafer. This mass production greatly reduces the price of individual devices. Thus, MEMS devices are relatively less expensive than their macro-world counterparts. In addition, cumbersome electrical components are typically not needed with MEMS devices, since the electronics can be placed directly on the MEMS device. This integration also has the advantage of picking up less electrical noise, thus improving the precision and sensitivity of sensors. As discussed above, MEMS devices provide some of the functionality of analytical instrumentation, but with vastly reduced cost, size, and power consumption, and an ability for real-time, in situ measurement.

Examples of micro-electromechanical systems are disclosed in U.S. Pat. No. 6,127,811 to Shenoy et al.; U.S. Pat. No. 6,288,534 to Starkweather et al.; U.S. Pat. No. 6,092,422 to Binnig et al.; U.S. Patent Application No. US 2001/0020166 PCT filed Apr. 30, 1997; Microtechnology in Modern Health Care by P. Detemple, W. Ehrfeld, H. Freimuth, R. Pommersheim, and P. Wagler in Medical Device Technology, November 1998; and Microelectromechanical Systems (MEMS): Technology, Design and Applications, coordinator: Lee, Abraham, University of California, Los Angeles, Department of Engineering, Information Systems and Technical Management, Short Course Program, Engineering 823.53, May 19-22, 1997, the entire contents of each of which are incorporated herein by reference.

Accordingly, a need exists for surgical instruments that can sense a multitude of parameters and factors, such as, for example, the distance between the tissue contacting surfaces of the surgical instrument. Such a surgical instrument can, according to the conditions sensed and/or measured, utilize, display, record and/or automatically control the position of the tissue contacting surfaces of the surgical instrument or alert a surgeon prior to operation of the surgical instrument.

In view of the foregoing, the need exists for the use of micro-electromechanical systems in combination with the surgical instruments and systems and, in particular in stapling instruments and energy based surgical instruments for monitoring, controlling and regulating conditions and/or parameters associated with the performance of various mechanical, electro-mechanical and electrosurgical procedures.

SUMMARY

The present invention is direct to surgical instruments including an end effector configured and adapted to engage tissue, and at least one micro-electromechanical system (MEMS) device operatively connected to the surgical instrument for at least one of sensing a condition, measuring a parameter and controlling the condition and/or parameter adjacent the end effector. The at least one MEMS device is operatively connected to the end effector. The at least one MEMS device is at least one of a pressure sensor, a strain sensor, a displacement sensor, an optical sensor, a biosensor, a temperature sensor, a torque sensor, an accelerometer, a flow sensor, an electrical sensor and a magnetic sensor for at least one of sensing, measuring and controlling the associated condition and/or parameter.

It is contemplated that the surgical instrument is a surgical stapler and the end effector includes a staple cartridge assembly, and an anvil operatively associated with the staple cartridge, the staple cartridge and the anvil being movably connected to one another to bring one into juxtaposition relative to the other. Each of the staple cartridge and the anvil define tissue contacting surfaces and the at least one MEMS device is operatively connected to at least one of the tissue contacting surface of the staple cartridge and the tissue contacting surface of the anvil. A plurality of MEMS devices are connected to the surgical instrument, the MEMS devices being configured and adapted to measure distance between the tissue contacting surface of the staple cartridge assembly and the tissue contacting surface of the anvil.

The MEMS devices can be configured and adapted to measure the amount of pressure applied to tissue clamped between the tissue contacting surface of the staple cartridge and the tissue contacting surface of the anvil. The MEMS devices are configured and adapted to measure the thickness of the tissue clamped between the tissue contacting surface of the staple cartridge and the tissue contacting surface of the anvil.

It is envisioned that the end effector is configured and adapted to perform an anastomosis. The surgical instrument can be a linear stapler that is adapted to perform an endoscopic gastrointestinal anastomosis. It is further contemplated that the surgical instrument is an annular stapler that is adapted to perform an end-to-end anastomosis.

It is envisioned that the end effector is a jaw mechanism including a pair of jaw members pivotably coupled to the distal end of the elongate shaft. It is further envisioned that at least one MEMS device is provided on at least one of the pair of jaw members. The MEMS devices are provided at least at one of a proximal end, a distal end and along a length of each of the pair of jaw members.

It is envisioned that the jaw mechanism is configured and adapted to perform an electrosurgical function. The jaw mechanism is configured and adapted to deliver electrosurgical energy to a target surgical site.

It is further envisioned that the surgical instrument is operatively couplable to a robotic system, wherein the end effector is configured and adapted to be remotely operated by the robotic system.

It is contemplated that the surgical instrument can include a loading unit having a proximal end and a distal end, the proximal end being selectively removably connected to the surgical instrument, the end effector is operatively connected to and part of the loading unit, and the loading unit includes the at least one MEMS device.

The end effector can be a surgical stapler including a staple cartridge assembly, and an anvil operatively associated with the staple cartridge assembly, the staple cartridge assembly and the anvil being movable and juxtaposable relative to one another. Each of the staple cartridge assembly and the anvil define tissue contacting surfaces and wherein at least one MEMS device is operatively connected to the at least one of the tissue contacting surface of the staple cartridge assembly and the tissue contacting surface of the anvil.

The MEMS devices are configured and adapted to measure distance between the tissue contacting surface of the staple cartridge assembly and the tissue contacting surface of the anvil. The MEMS devices are configured and adapted to measure at least one of the amount of pressure applied to tissue and the thickness of tissue clamped between the tissue contacting surface of the staple cartridge assembly and the tissue contacting surface of the anvil.

The loading unit can include an elongate shaft having a distal end, the end effector being operatively connected to a distal end of an elongate shaft and the staple cartridge and the anvil are oriented transversely with respect to the elongate shaft.

It is envisioned that the end effector is configured and adapted to perform an anastomosis. It is further envisioned that the end effector is a jaw mechanism including a pair of jaw members pivotably coupled to the distal end of the elongate shaft. The at least one MEMS device is provided on at least one of the pair of jaw members. The MEMS devices can be provided at least at one of a proximal end, a distal end and along a length of each of the pair of jaw members.

It is envisioned that the jaw mechanism is configured and adapted to perform an electrosurgical function. The jaw mechanism can be configured and adapted to deliver electrosurgical energy to the target surgical site.

It is envisioned that each of the plurality of MEMS devices is electrically connected to a control box via a lead wire extending from the housing.

The surgical instrument can further include a control box electrically connected to each of the plurality of MEMS devices via at least one wire lead.

According to another aspect of the present invention, there is provided a robotic system for performing surgical tasks a frame, a robotic arm connected to the frame and movable relative to the frame, an actuation assembly operatively associated with the robotic arm for controlling operation and movement of the robotic arm, a loading unit including an elongate shaft operatively connected to the robotic arm, and an end effector operatively coupled to a distal end of the elongate shaft and configured to engage tissue, and at least one micro-electromechanical system (MEMS) device operatively connected to the loading unit for at least one of sensing a condition, measuring a parameter and controlling the condition and/or parameter adjacent the end effector.

The at least one MEMS device is at least one of a pressure sensor, a strain sensor, a displacement sensor, an optical sensor, a biosensor, a temperature sensor, a torque sensor, an accelerometer, a flow sensor, an electrical sensor and a magnetic sensor for at least one of sensing, measuring and controlling an associated condition and/or parameter.

In one embodiment the end effector includes a pair of jaw members movably coupled to the distal end of the elongate shaft. It is envisioned that a plurality of MEMS devices are provided on each of the pair of jaw members. Preferably, a plurality of MEMS devices are provided at least at one of a proximal end, a distal end and along a length of each of the pair of jaw members.

The loading unit can be connected to the robotic arm via a bayonet-type connection.

In another embodiment, the end effector is configured and adapted to perform an electrosurgical function. Preferably, the end effector is configured and adapted to deliver electrosurgical energy to the target surgical site.

In yet another embodiment, the robotic system further includes a controller having a processor and a receiver for receiving electrical signals transmitted from the actuation assembly and for controlling the operation and movement of the loading unit.

The end effector can be a fastener applier, a surgical stapler, a vessel clip applier or a vascular suturing assembly.

As a surgical stapler, the end effector includes a staple cartridge assembly and an anvil operatively associated with the staple cartridge assembly and in juxtaposition relative to the staple cartridge assembly, and wherein at least one MEMS device is operatively connected to each of the staple cartridge assembly and the anvil. The staple cartridge assembly defines a tissue contacting surface and wherein at least one MEMS device is operatively connected to the tissue contacting surface of the staple cartridge assembly. The anvil defines a tissue contacting surface and wherein at least one MEMS device is operatively connected to the tissue contacting surface of the staple cartridge.

The MEMS devices can be configured and adapted to measure distance between the tissue contacting surface of the staple cartridge assembly and the tissue contacting surface of the anvil. Alternatively, the MEMS devices can be are configured and adapted to measure the amount of pressure applied to tissue clamped between the tissue contacting surface of the staple cartridge assembly and the tissue contacting surface of the anvil.

The staple cartridge assembly and the anvil are desirably transversely oriented with respect to the elongate shaft. It is envisioned that the staple cartridge assembly and the anvil are pivotably connected to the distal end of the elongate shaft.

As a vessel clip applier, the end effector includes a body portion having a distal end and a proximal end, wherein the proximal end is operatively connectable to the robotic arm, and a jaw assembly operatively connected to the distal end of the body portion, wherein the jaw assembly includes a first and a second jaw portion. Each of the first and the second jaw portions includes at least one MEMS device operatively connected thereto.

As a vascular suturing assembly, the end effector includes an elongate body having a distal end and a proximal end, wherein the proximal end in operatively connectable to the robotic arm, and a pair of needle receiving jaws pivotably mounted to the distal end of the elongate body portion, the pair of needle receiving jaws being configured and adapted to pass a surgical needle and associated length of suture material therebetween. Preferably, at least one MEMS component is operatively connected to each of the pair of needle receiving jaws.

According to yet another aspect of the present invention a loading unit for use with a surgical instrument is provided and includes an elongate tubular shaft having a proximal end and a distal end, an end effector operably connected to the distal end of the tubular shaft, a connector for connecting the proximal end of the tubular shaft to a surgical instrument, and at least one micro-electromechanical system (MEMS) device operatively connected to the loading unit for at least one of sensing a condition, measuring a parameter and controlling the condition and/or parameter adjacent the end effector.

It is envisioned that at least one MEMS device is operatively connected to the end effector. The MEMS device can be at least one of a pressure sensor, a strain sensor, a displacement sensor, an optical sensor, a biosensor, a temperature sensor, a torque sensor, an accelerometer, a flow sensor, an electrical sensor and a magnetic sensor for at least one of sensing, measuring and controlling an associated condition and/or parameter.

It is contemplated that the surgical instrument is a surgical stapler and the end effector includes a staple cartridge assembly and an anvil operatively associated with the staple cartridge, the staple cartridge and the anvil being movably connected to one another to bring one into juxtaposition relative to the other. Each of the staple cartridge and the anvil define tissue contacting surfaces and the at least one MEMS device is operatively connected to at least one of the tissue contacting surface of the staple cartridge and the tissue contacting surface of the anvil.

It is envisioned that a plurality of MEMS devices connected to the surgical instrument, the MEMS devices being configured and adapted to measure distance between the tissue contacting surface of the staple cartridge assembly and the tissue contacting surface of the anvil. It is further envisioned that the MEMS devices are configured and adapted to measure the amount of pressure applied to tissue clamped between the tissue contacting surface of the staple cartridge and the tissue contacting surface of the anvil. It is still further envisioned that the MEMS devices are configured and adapted to measure the thickness of the tissue clamped between the tissue contacting surface of the staple cartridge and the tissue contacting surface of the anvil.

The end effector can be configured and adapted to perform an anastomosis. The surgical instrument can be a linear stapler that is adapted to perform an endoscopic gastrointestinal anastomosis. The surgical instrument can be an annular stapler that is adapted to perform an end-to-end anastomosis.

It is envisioned that the end effector is a jaw mechanism including a pair of jaw members pivotably coupled to the distal end of the elongate shaft. At least one MEMS device can be provided on at least one of the pair of jaw members. The MEMS devices can be provided at least at one of a proximal end, a distal end and along a length of each of the pair of jaw members.

It is contemplated that at least one MEMS device is a temperature sensing MEMS device. The temperature sensing MEMS device is positioned on and/or encapsulated in thermally conductive tips or elements, wherein the conductive tips are semi-rigid wires made of shape memory metal for a particular application, wherein the conductive tips are extendable out from the loading unit and into the tissue adjoining the loading unit in order to monitor temperature of the tissue adjoining the loading unit.

According to another aspect of the present invention, a surgical instrument for use with a loading unit that is operatively couplable to the surgical instrument and has an end effector with a pair of juxtaposable jaws for performing a surgical function, the end effector having at least one micro-electromechanical system (MEMS) device operatively connected thereto for at least one of sensing a condition, measuring a parameter and controlling the condition and/or parameter adjacent the end effector. The surgical instrument includes a housing, an elongate shaft that extends from the housing and has a distal end operatively couplable to a loading unit of the above type, an approximation mechanism for approximating the pair of jaws, an actuation mechanism for activating the jaws to perform the surgical function, and at least one micro-electromechanical system (MEMS) device operatively connected to the surgical instrument for at least one of sensing a condition, measuring a parameter and controlling the condition and/or parameter adjacent the end effector and for cooperative operation with the at least one MEMS of the end effector.

It is an object of the present disclosure to provide mechanical, electro-mechanical and energy based surgical instruments and systems having micro-electromechanical devices associated therewith to monitor, control, measure and/or regulate conditions and parameters associated with the performance and operation of the surgical instrument.

It is a further object of the present disclosure to provide improved mechanical, electro-mechanical and energy based surgical instruments and systems which are more effective, safer and/or easier to use than similar conventional surgical instruments and systems.

It is another object of the present disclosure to provide improved mechanical, electro-mechanical and energy based surgical instruments and systems which better control the effects they have on target tissue and on the patient.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3 is a perspective view of yet another surgical stapling instrument incorporating micro-electromechanical system devices in accordance with the present disclosure;

FIG. 3A is an enlarged perspective view of a distal end of the surgical stapling instrument of FIG. 3;

FIG. 6A is an enlarged perspective view of the indicated region of the surgical instrument depicted in FIG. 6;

DETAILED DESCRIPTION OF PREFERRED EMBODIMENTS

Figure 1:
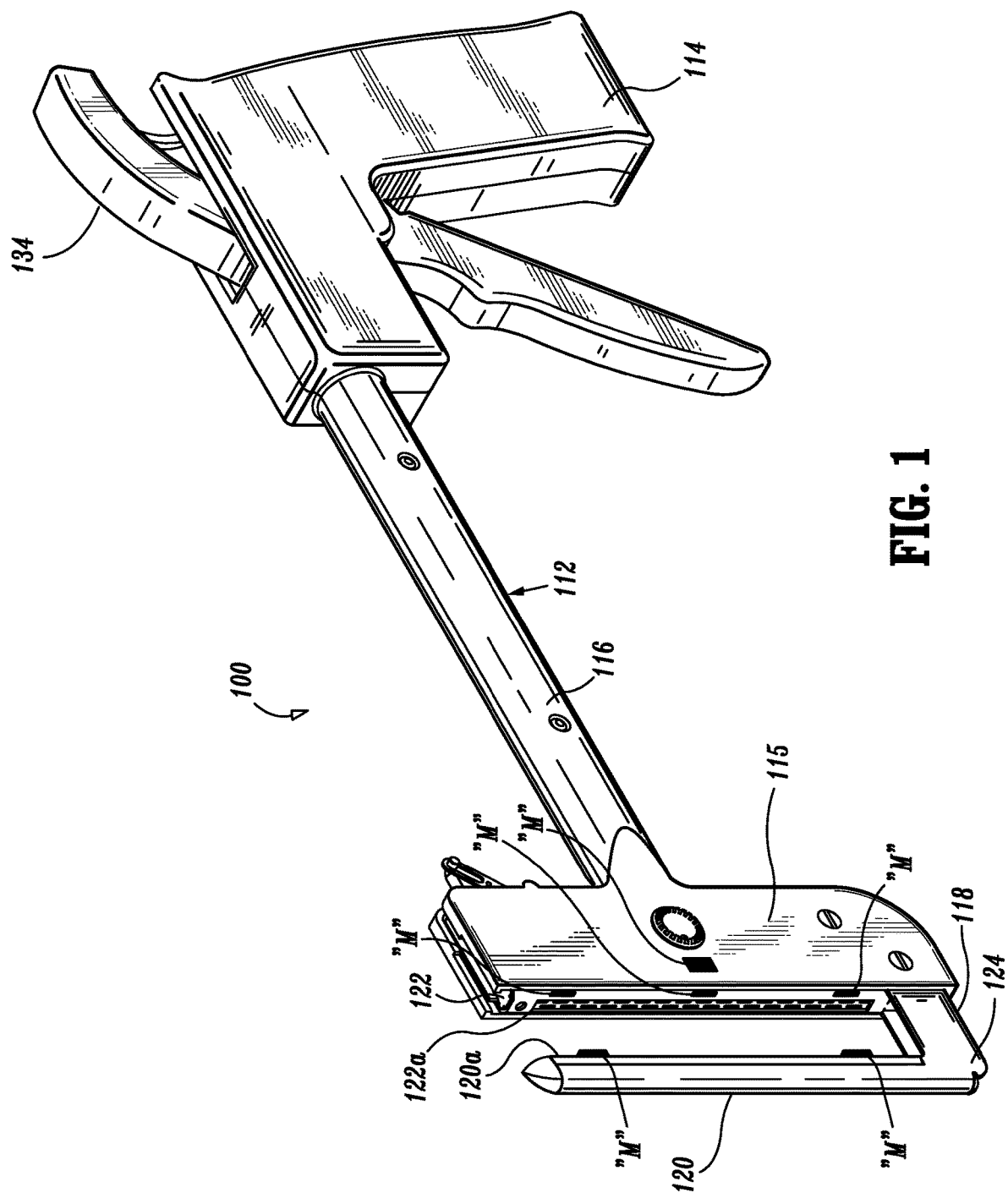
FIG. 1 is a perspective view of a surgical stapling instrument incorporating micro-electromechanical system devices, in accordance with the present disclosure.

Preferred embodiments of the presently disclosed surgical instruments and systems will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

In accordance with the present disclosure, a micro-electromechanical system (MEMS) is used to provide highly miniaturized MEMS devices and/or systems capable of performing various functions, e.g., sensing, monitoring, controlling, influencing, regulating and/or measuring various conditions and/or parameters of surgical instruments and systems, such as, for example, the distance between and/or the pressure applied by the jaws of an end effector. In the present disclosure, "controlling" is meant to include influencing and/or regulating. The MEMS devices and/or systems can also provide feedback for automatic (remote or manual) control of the operation of the surgical instrument.

MEMS devices have the required very small size, low power requirements, and ability to be readily integrated with standard electrical systems. These characteristics make MEMS devices ideal for incorporation into and/or on surgical instruments and systems. As will be described in greater detail below, MEMS devices can be utilized in conjunction with, and incorporated into and/or on various portions and structural elements of surgical instruments and systems.

MEMS devices and/or systems considered to be within the scope of the present disclosure, include, for example, MEMS sensors and/or sensor devices, actuator MEMS devices (motors, hydraulics, pumps, ultrasonic devices, etc.), fluid moving and mixing components, heaters, and diagnostic MEMS devices for measuring physiologic parameters and tissue properties, such as the integrity of a staple line or of a repaired or joined tissue by measuring fluid, e.g., blood flow and/or presence, and electrical signals or pressure within the stapled tissue.

Also considered within the scope of this disclosure are: types of MEMS devices and/or systems used to determine and/or measure distance including capacitive, magnetic (Hall Effect sensors, for measuring the strength of the magnetic field between one or more magnets), light or radio frequency (RF) emitting/receiving, and optical fiber interferometric sensors; types of MEMS devices and/or systems used to determine and/or measure the amount of pressure applied to tissue including capacitive, piezoelectric, piezoresistive, resonant, light or RF emitting/receiving, and optical fiber interferometric sensors; and types of MEMS devices and/or systems used to determine and/or measure tissue thickness, and to determine or measure pressure and/or to provide pressure data to a processor which correlates the pressure data with tissue thickness using a look-up table or other data structure. By knowing the tissue thickness, the surgeon can then determine the proper size of the staples and/or tissue gap between the tissue contacting surfaces of the anvil and staple cartridge before performing the stapling procedure.

While MEMS devices and/or systems are preferred, it is within the scope of the present disclosure and envisioned that other types of devices and/or systems can be used with or without MEMS devices and/or systems to determine and/or measure various conditions and/or parameters.

In a preferred configuration, the surgical instrument can include one or more transducer MEMS delivery devices and/or systems capable of being powered by a battery for generating RF or other types of signals. These transducer MEMS delivery devices are aligned with transducer MEMS receiving devices capable of receiving the generated signals. Accordingly, the distance between the transducer MEMS delivery and receiving devices can be measured by a processor correlating the transmission time of the generated RF signals with distance using a data structure. By knowing the distance, the processor can then compute the thickness of the tissue clamped by the surgical instrument.

Further, when the transducer MEMS delivery and/or receiving devices press upon the tissue clamped by the surgical instrument, pressure from the tissue is applied to the transducer MEMS delivery and/or receiving devices and/or systems. The transducer MEMS delivery and/or receiving devices and/or systems in turn determine the applied pressure and output signals.

Alternatively, one or more transducer MEMS delivery and/or receiving components, capable of generating and receiving signals reflected off a target, can be provided on the anvil and/or the staple cartridge in order to determine the distance between the tissue contacting surfaces of the anvil and the staple cartridge for determining if the staple cartridge should be fired.

Preferably, circuitry of the MEMS devices and/or systems amplifies the signals, before being transmitted to standard electrical components or to the processor, for analysis using conventional algorithms implemented as a set of programmable instructions. The processor analyzes the reading to determine if the reading is within the desired limits for the surgical instrument and/or the current application. The processor can use at least one or more comparators to compare the value of the determined reading with stored, predetermined values.

If the determined reading is within the desired limits for the surgical instrument, then the surgical instrument can be fired as usual. However, if the reading is outside of the desired limits, the surgical instrument and/or the operator can: (1) prevent the firing of the surgical instrument until the reading is within the desired limits; (2) adjust the components of the surgical instrument in order to alter the reading as needed; (3) alert the operator; and/or (4) wait a few moments and then take the reading again.

Further, the measured readings received from the MEMS devices and/or systems can also be used to control the firing of the surgical instrument. For example, if the tissue thickness is large, the firing of the surgical instrument can be automatically or manually adjusted in order for the surgical instrument to be fired with sufficient power to affect all of the tissue. The reading of tissue thickness can also be used by a surgeon to determine whether the power applied by the surgical instrument is large enough to penetrate and affect all of the tissue.

The MEMS devices and/or systems are preferably positioned at opposing or juxtaposed locations when used to measure and/or determine distances. The MEMS devices are also preferably positioned on tissue contacting surfaces of the surgical instrument in order to measure and/or determine a distance between the tissue contacting surfaces of the surgical instrument as one or more structural components of the surgical instrument is/are moved relative to one another. It is further envisioned that MEMS devices and/or systems are capable of measuring and/or determining a thickness of tissue clamped between the tissue contacting surfaces of the surgical instrument.

Other types of MEMS devices and/or systems that can be used within the scope of the present disclosure include strain, optical, flow, electrochemical and bio-sensors. Optical sensors for fluorescence and absorption for determining, for example, the presence of blood glucose, and hence, the presence of blood, require fiber optic connections to photodetectors and/or photomultiplier tubes that may or may not be miniaturized. Biosensors can be used to measure tissue characteristics before and/or after the stapling procedure. That is, bio-sensors can be used to ensure that the tissue is in condition or acceptable for stapling, or as a check after the staples have been fired to ensure that the tissue is healthy (e.g., has good blood flow, is healing properly, etc).

Turning now to FIGS. 1-4, specific embodiments of several representative surgical staplers including MEMS devices "M", in accordance with the present disclosure, are shown. As seen in FIG. 1, a first embodiment of a surgical stapler, here, a transverse anastomotic stapler, in accordance with the present disclosure, is shown generally as 100. Surgical stapler 100 includes a housing 112 including a stationary handle 114, a distally extending body portion 116 operatively connected to housing 112, and a transverse body portion 115 operatively connected to distally extending body portion 116. Transverse body portion 115 is configured and adapted to operatively receive a support frame 118 in a distal end thereof.

Surgical stapler 100 further includes an anvil 120 fastened to a first leg 124 or distal portion of support frame 118 and extending transversely across transverse body portion 115. Surgical stapler 100 further includes a staple cartridge assembly 122 operatively received within transverse body portion 115. Each of anvil 120 and staple cartridge assembly 122 include juxtaposed tissue contacting surfaces 120a, 122a, respectively. A trigger actuator 134 is operatively connected to handle 114 and is configured and adapted to distally advance staple cartridge assembly 122 toward anvil 120 in order to fire surgical stapler 100.

In accordance with the present disclosure, surgical stapler 100 includes a plurality of MEMS devices "M" provided at specific locations thereon. In particular, by way of example only and in no way is it to be considered as limiting, as seen in FIG. 1, MEMS devices "M" can preferably be provided along the length of tissue contacting surface 120a of anvil 120, along the length of tissue contacting surface 122a of staple cartridge assembly 122 and/or on staple cartridge assembly 122 and transverse body portion 115.

As described above, MEMS devices "M" enable, for example, the measurement of various parameters of surgical stapler 100, such as, for example, the distance between tissue contacting surfaces 120a and 122a of surgical stapler 100, as well as the amount of pressure applied to tissue clamped between tissue contacting surfaces 120a, 122a. It is further envisioned that MEMS devices "M" are capable of measuring and/or determining a thickness of the tissue clamped between tissue contacting surfaces 120a, 122a.

It is envisioned that MEMS devices "M" may transmit feedback signals of the measured and/or sensed parameters to a central processing unit "CPU" (e.g., control box 562 of FIG. 6) or actuation assembly 612 (see FIG. 7), via wire leads 560 (see FIG. 6) or transmission wires "W" (see FIG. 7), for further processing. Alternatively, it is contemplated that MEMS devices "M" can transmit feedback signals of the measured and/or sensed parameters to the CPU via wireless transmissions.

Reference is made to commonly assigned U.S. Pat. No. 5,964,394 to Robertson, the entire content of which is incorporated herein by reference, for a more detailed explanation of the operation of surgical stapler 100.

Figure 2:
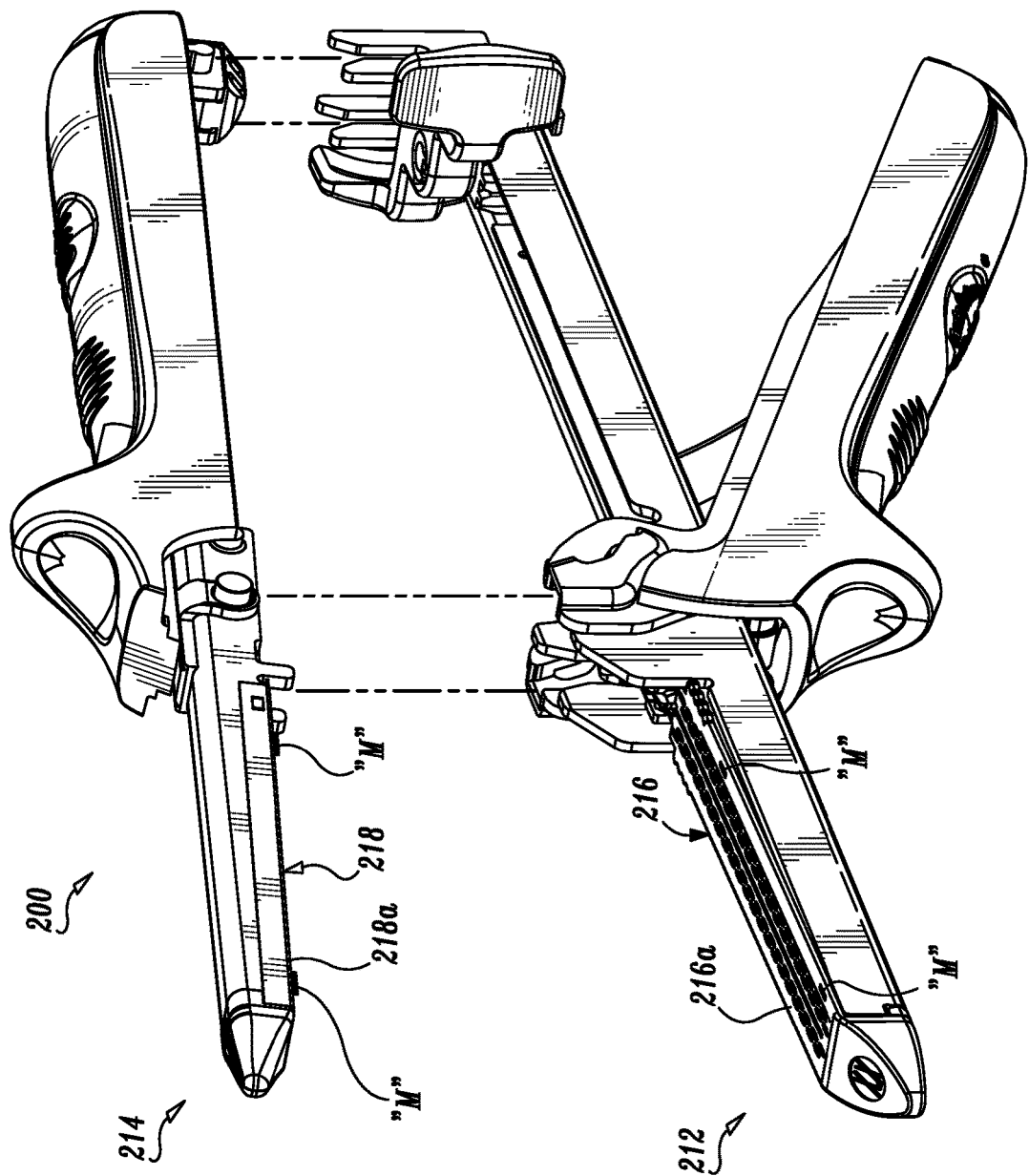
FIG. 2 is a partially exploded perspective view of an alternative surgical stapling instrument incorporating micro-electromechanical system devices in accordance with the present disclosure.

Turning now to FIG. 2, an alternative embodiment of a surgical stapler, here, an open gastrointestinal anastomotic stapler, in accordance with the present disclosure, is shown generally as 200. Surgical stapler 200 includes a cartridge receiving half-section 212, an anvil half-section 214 operatively couplable to cartridge receiving half-section 212, a staple cartridge assembly 216 configured and adapted to be removably mounted within a distal end of cartridge receiving half-section 212, and an anvil 218 operatively mounted to a distal end of anvil half-section 214. Staple cartridge assembly 216 includes a tissue contacting surface 216a and anvil 218 includes a tissue contacting surface 218a juxtaposed to tissue contacting surface 216a of staple cartridge assembly 216.

In accordance with the present disclosure, surgical stapler 200 includes a plurality of MEMS devices "M" provided at specific locations thereon. In particular, by way of example only and in no way is it to be considered as limiting, as seen in FIG. 2, MEMS devices "M" can preferably be provided along the length of or as shown, at specific locations on tissue contacting surface 218a of anvil 218, along the length of tissue contacting surface 216a of staple cartridge assembly 216, on the distal end portions of cartridge receiving half-section 212 and anvil half-section 214.

As described above, MEMS devices "M" enable the measurement of various parameters of surgical stapler 200, such as, for example, the distance between tissue contacting surfaces 216a and 218a of surgical stapler 200, as well as the amount of pressure applied to tissue clamped between tissue contacting surfaces 216a, 218a of surgical stapler 200.

Reference is made to commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference, for a more detailed explanation of the operation of surgical stapler 200.

Turning now to FIGS. 3 and 3A, yet another embodiment of a surgical stapler, here, an endoscopic gastrointestinal anastomotic stapler, in accordance with the present disclosure, is shown generally as 300. Briefly, surgical stapler 300 includes a handle assembly 312 and an elongated body 314. A disposable loading unit or DLU 316 is releasably secured to a distal end of elongated body 314. Disposable loading unit 316 includes an end effector 317 having a staple cartridge assembly 318 housing a plurality of surgical staples (not shown) and an anvil 320 movably secured in relation to staple cartridge assembly 318. Staple cartridge assembly 318 includes a tissue contacting surface 318a and anvil 320 includes a tissue contacting surface 320a juxtaposed to tissue contacting surface 318a of staple cartridge assembly 318.

Handle assembly 312 includes a stationary handle member 322, a movable handle member 324 and a barrel portion 326. A rotatable member 328 is preferably mounted on the forward end of barrel portion 326 to facilitate rotation of elongated body 314 with respect to handle assembly 312. An articulation lever 330 is also preferably preferably mounted on the forward end of barrel portion 326 adjacent rotatable knob 328 to facilitate articulation of end effector 317.

In accordance with the present disclosure, surgical stapler 300 includes a plurality of MEMS devices "M" provided at specific locations thereon. In particular, by way of example only and in no way is it to be considered as limiting, as seen in FIGS. 3 and 3A, MEMS devices "M" can be provided preferably along the length of tissue contacting surface 320a of anvil 320, along the length of tissue contacting surface 318a of staple cartridge assembly 318, on disposable loading unit 316, on elongated body 314 and/or on handle assembly 312.

As described above, MEMS devices "M" enable the measurement of various parameters of surgical stapler 300, such as, for example, the distance between tissue contacting surfaces 318a and 320a of surgical stapler 300, as well as the amount of pressure applied to tissue clamped between tissue contacting surfaces 318a, 320a of surgical stapler 300.

In another preferred configuration, as shown in FIGS. 3 and 3A, MEMS devices "M" are positioned in proximity to a pivot point of anvil 320 and staple cartridge assembly 318 of surgical stapler 300. Other MEMS devices "M" are positioned remotely from the pivot point. It is envisioned that the MEMS devices "M" positioned on anvil 320 and staple cartridge assembly 318 can be of the type capable of emitting light from laser diodes or from a fiber optic waveguide. In particular, a MEMS device in the form of a MEMS light producing sensor/device (e.g., bicell or photodiode) is positioned opposite an aforementioned MEMS device for detecting changes in the amount of light being received as a result of the changing angle of rotation between anvil 320 and staple cartridge 318.

Accordingly, in use, if the amount of light being received is high, a MEMS light producing device and its corresponding MEMS light detection device are close to each other. Accordingly, the distance between anvil 320 and staple cartridge assembly 318 is small, and, if there is any tissue clamped between anvil 320 and staple cartridge assembly 318, the thickness of the tissue is also small. If the amount of light being received is low, the MEMS light producing device and its corresponding MEMS light detection device are further from each other. Accordingly, the distance between anvil 320 and staple cartridge assembly 318 is large, and, if there is any tissue clamped between anvil 320 and staple cartridge assembly 318, the thickness of the tissue is also large.

Distance and tissue thickness can also be determined by timing the duration until the MEMS light detection device senses light once the MEMS light producing device is turned on. If the MEMS light detection device senses light, for example, at time to after the MEMS light producing device is turned on, then anvil 320 and staple cartridge assembly 318 are in close proximity or touching (small tissue thickness). If the MEMS light detection device senses light, for example, at time $t_0+t_1$ after the MEMS light producing device is turned on, then anvil 320 and staple cartridge assembly 318 are at a predetermined distance from each other. Also, if there is any tissue clamped between anvil 320 and staple cartridge assembly 318, then the tissue thickness is a predetermined tissue thickness. The predetermined distance and tissue thickness can be determined by a processor accessing one or more look-up tables or other data structures and correlating the measured time to distance and, then correlating the distance to tissue thickness.

Reference is made to commonly assigned U.S. Pat. Nos. 5,865,361, 6,330,965 and 6,241,139 to Milliman et al., the entire contents of which are incorporated herein by reference, for a more detailed explanation of the operation of surgical stapler 300.

Figure 4:
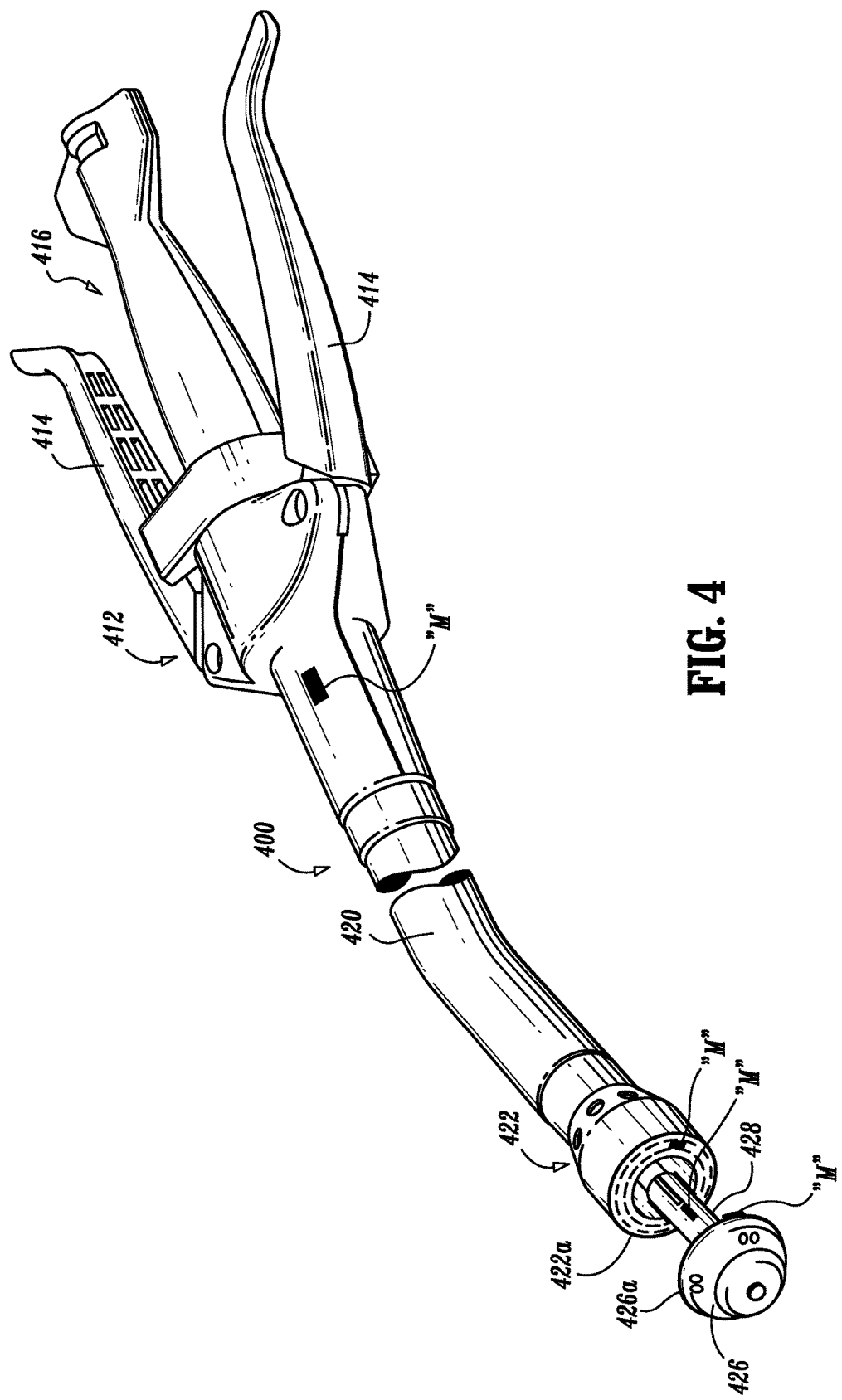
FIG. 4 is a perspective view of still another surgical stapling instrument incorporating micro-electromechanical system devices in accordance with the present disclosure.

Turning now to FIG. 4, an alternative embodiment of a surgical stapler, in accordance with the present disclosure, is shown generally as 400. Briefly, surgical stapler 400 includes a handle assembly 412 having at least one pivotable actuating handle member 414 and an advancing member 416 configured and adapted to open and close surgical stapler 400. Surgical stapler 400 further includes a tubular body portion 420 extending from handle assembly 412, an annular staple cartridge assembly 422 operatively connected to a distal end of tubular body portion 420, and an annular anvil 426 positioned opposite staple cartridge assembly 422 and connected to surgical stapler 400 by a shaft 428. Staple cartridge assembly 422 includes a tissue contacting surface 422a and anvil 426 includes a tissue contacting surface 426a in juxtaposition relative to tissue contacting surface 422a of staple cartridge assembly 422.

In accordance with the present disclosure, surgical stapler 400 includes a plurality of MEMS devices "M" provided at specific locations thereon. In particular, by way of example only and in no way is it to be considered as limiting, as seen in FIG. 4, at least one MEMS device "M" can be provided preferably on tissue contacting surface 426a of anvil 426, tissue contacting surface 422a of staple cartridge assembly 422, on shaft 428 and/or on handle assembly 412.

As described above, MEMS devices "M" enable the measurement of various parameters of surgical stapler 400, such as, for example, the distance between tissue contacting surfaces 422a and 426a of surgical stapler 400, as well as the amount of pressure applied to tissue clamped between tissue contacting surfaces 422a, 426a of surgical stapler 400.

Reference is made to commonly assigned U.S. Pat. No. 5,915,616 to Viola et al., the entire content of which is incorporated herein by reference, for a more detailed explanation of the operation of surgical stapler 400.

While MEMS devices for determining distance and/or pressure are shown located at certain discrete positions on the structural elements of the surgical staplers shown in FIGS. 1-4, it is within the scope of the present disclosure that MEMS devices for determining distance and/or pressure can be positioned anywhere on the structural elements of the surgical staplers.

In FIGS. 1-4, MEMS devices "M" are merely located at representative positions and are not intended to be indicative of the only positions where MEMS devices "M" can be provided or the numbers of MEMS devices "M" that can be provided. It is envisioned that a staple cartridge holding component of the surgical stapler, including a staple cartridge, can be automatically or manually moved away from an anvil if the pressure applied to the clamped tissue is above a predetermined threshold. The surgical stapler can also be automatically or manually prevented from being fired in response to the feedback provided by MEMS devices "M". The feedback provided by MEMS devices "M" could be in the form of feedback signals (e.g., audio, visual and/or audiovisual), and/or in the form of mechanical feedback (e.g., a tactile indication).

The surgical staplers disclosed herein can be fitted with different-sized surgical staples (i.e., staples having varying length legs) and can be adapted to automatically select the proper sized staples for performing a or the particular surgical procedure according to information obtained by the MEMS devices "M".

Figure 5A:
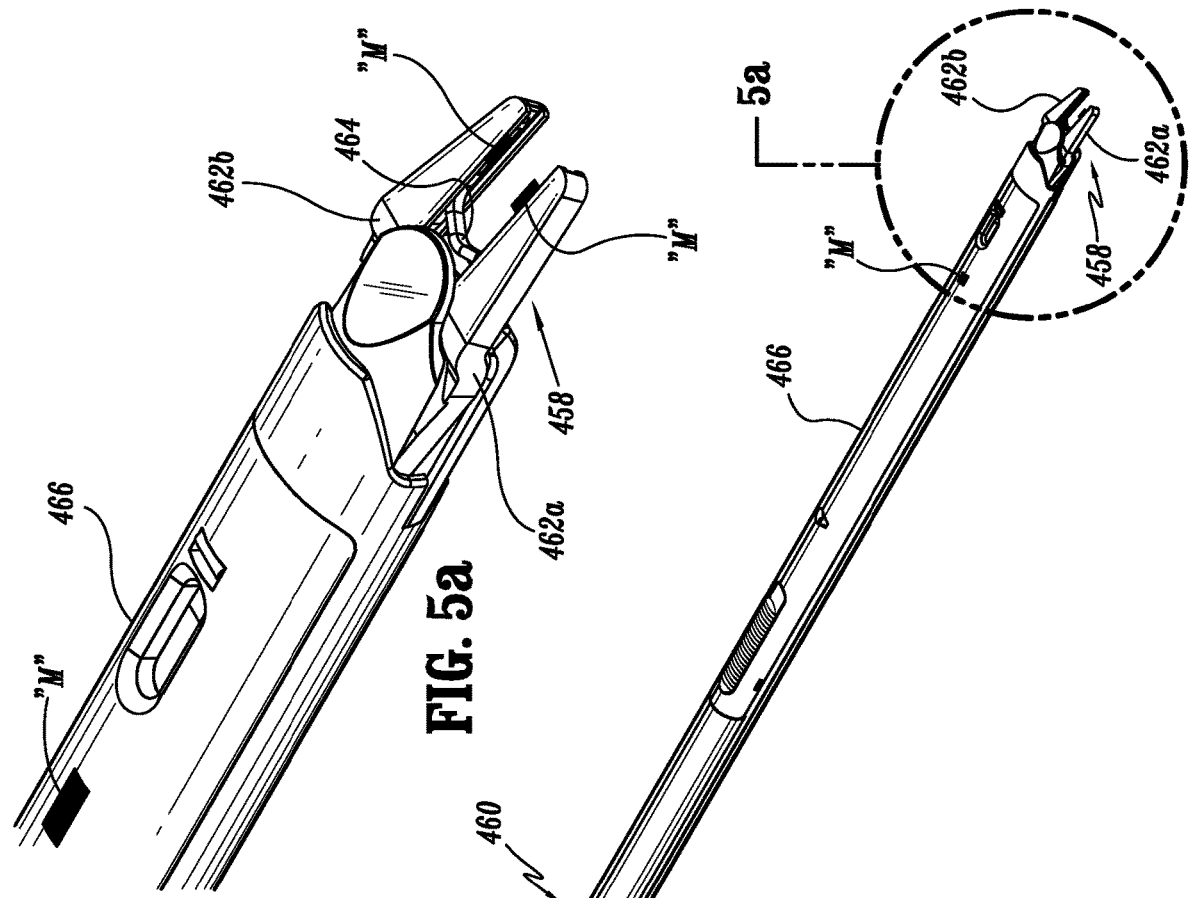
FIG. 5A is an enlarged perspective view of the indicated region of the surgical instrument depicted in FIG. 5.
Figure 5:
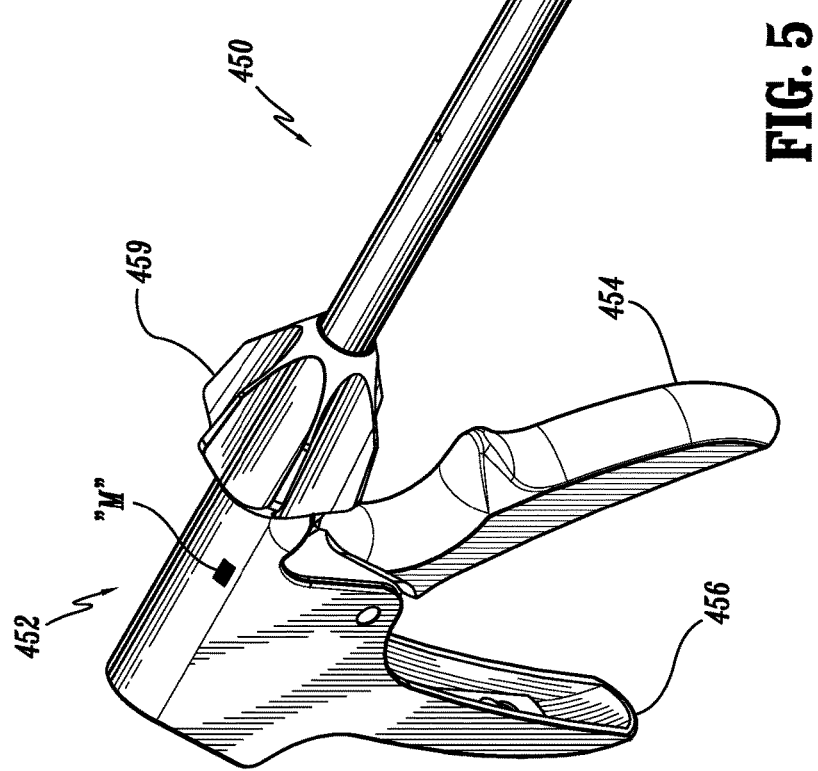
FIG. 5 is a perspective view of a surgical instrument for placing clips in laparoscopic or endoscopic procedures incorporating micro-electromechanical system devices in accordance with the present disclosure.

Turning now to FIGS. 5 and 5A, in which like reference numerals identify similar or identical elements, a surgical instrument for placing clips in laparoscopic or endoscopic procedures employing the novel features of the present disclosure is generally designated with the reference numeral 450.

As seen in FIG. 5, surgical instrument 450 includes a handle portion 452 having pivoting or movable handle 454 and stationary handle 456. Manipulation of handles 454, 456 actuates a tool assembly, such as a jaw assembly 458, through elongated body 460 which extends distally from handle portion 452. Elongated body 460 is preferably rotatable with respect to handle portion 452 by turning knob 459. Jaw assembly 458 includes first and second juxtaposed jaw portions 462a, 462b, respectively, which are simultaneously movable between a substantially approximated position, in which jaw portions 462a and 462b are in relatively close relation to one another, and a spaced position, in which jaw portions 462a and 462b are separated at least a sufficient distance to receive an unformed surgical clip 464 (see FIG. 5A) therebetween.

It is envisioned that a plurality of surgical clips 464 are stored in a loading unit 466 which is releasably mounted to elongated body 460. In a preferred embodiment, loading unit 466 is disposable (i.e., in the form of a disposable loading unit or "DLU") subsequent to depletion of the supply of surgical clips 464 stored therein. The remainder of surgical instrument 450 may be disassembled, resterilized and reused in combination with another loading unit containing a supply of surgical clips 464.

In use, approximation of movable handle 454 toward stationary handle 456 results in the advancement of a distal-most surgical clip 464 to a position between jaw portions 462a and 462b. Further approximation of handles 454, 456 toward one another results in the approximation of jaw portions 462a and 462b toward one another to form the surgical clip disposed therebetween.

In accordance with the present disclosure, surgical instrument 450 includes a plurality of MEMS devices "M" provided at specific locations thereon. In particular, by way of example only and in no way is it to be considered limiting, as seen in FIGS. 5 and 5A, at least one MEMS device "M" can be provided preferably on the tissue contacting surface of at least one, preferably each, jaw portion 462a, 462b of jaw assembly 458, on loading unit 466 and/or elongated body 460, and/or on handle portion 452.

As described above, MEMS devices "M" enable the measurement of various parameters of surgical instrument 450, such as, for example, the distance between the tissue contacting surfaces of jaw portions 462a, 462b, as well as the amount of pressure applied to tissue clamped between jaw portions 462a, 462b. It is further envisioned that MEMS devices "M" are capable of measuring and/or determining a thickness of the tissue clamped between tissue contacting surfaces of jaw portions 462a, 462b.

Reference is made to commonly assigned U.S. Pat. No. 6,059,799 to Aranyi et al., the entire content of which is incorporated herein by reference, for a more detailed explanation of the operation of surgical instrument 450.

Figure 6:
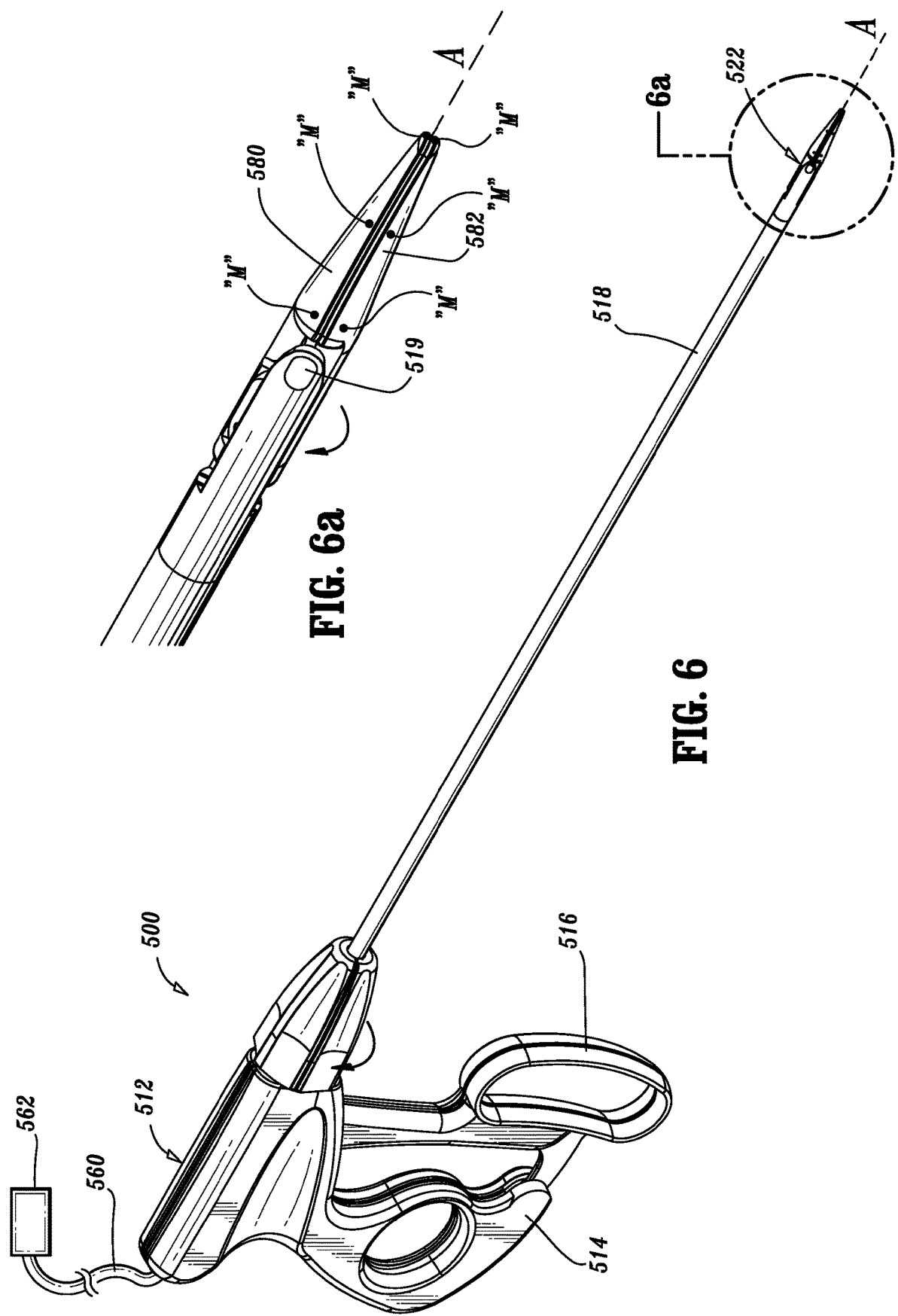
FIG. 6 is a perspective view of an energy-based surgical instrument incorporating micro-electromechanical system devices in accordance with the present disclosure.

Turning now to FIGS. 6 and 6A, in which like reference numerals identify similar or identical elements, a surgical instrument employing the novel features of the present disclosure is generally designated with the reference numeral 500.

As seen in FIG. 6, surgical instrument 500 includes a housing 512 having a fixed handle portion 514, a movable handle portion 516, an elongated shaft 518 extending distally from housing 512, and a jaw mechanism 522 operatively coupled to a distal end of shaft 518. As seen in detail in FIG. 6A, jaw mechanism 522 includes a pair of jaw members 580, 582 which are pivotable about pin 519 in order to provide the opening and closing of jaw mechanism 522. Surgical instrument 500 is configured and adapted such that, in operation, manipulation of movable handle portion 516, distally and proximally, relative to fixed handle portion 514, causes jaw members 580, 582 of jaw mechanism 522 to open and close. Jaw members 580, 582 are shown as being configured and adapted to perform an electrosurgical function, such as, for example, coagulation, cauterization and the like.

Jaw mechanism 522 can be configured to grasp, staple, cut, retract, coagulate and/or cauterize. The above examples are merely intended to be illustrative of a few of the many functions which jaw mechanism 522 can be configured to accomplish and in no way is intended to be an exhaustive listing of all of the possible jaw or like or pivotable structures.

As further shown in FIG. 6A, jaw mechanism 522 is provided with a plurality of micro-electrosurgical system (MEMS) devices "M" placed at specific desired locations on, in or along the surfaces of jaw members 580, 582. For example, MEMS devices "M" can be placed near a proximal end and/or near a distal end of jaw members 580, 582, as well as along the length of jaw members 580, 582.

In one preferred embodiment of the present disclosure, MEMS devices "M" offer a solution for controlling the amount of energy delivered, by radio frequency (e.g., monopolar or bipolar), ultrasonic, laser, argon beam or other suitable energy systems, to tissue during treatment with energy based electrosurgical instruments, for example, electrocautery surgical instruments. In electrocautery surgical instruments the degree of tissue cutting, coagulation and damage are influenced by the power setting, the force applied by the jaw mechanism of the electrocautery surgical instrument to the tissue, the duration of contact between the jaw mechanism of the electrocautery surgical instrument and the tissue, as well as other factors.

Accordingly, it is contemplated that energy sensing MEMS devices "M", capable of measuring and/or sensing energy, be used to monitor, control, measure and/or regulate the amount of energy delivered by surgical instrument 500 to the tissue. Energy sensing MEMS devices "M" can provide feedback to electronics within the electrocautery instrument, for example, to create a more consistent desired tissue effect. In particular, it is envisioned that selected MEMS devices "M" are configured and adapted to be force and/or pressure sensing MEMS devices so that a pressure or a gripping force applied to the tissue by jaw members 580, 582 can be sensed and regulated.

It is further envisioned that selected MEMS devices "M" can be configured and adapted to measure temperature on or near an active blade (not shown) of surgical instrument 500 (i.e., an electrocautery instrument, electrosurgical pencil, etc.). These temperature sensing MEMS devices "M" can be used to monitor and control the temperature of the active blade of the electrocautery instrument, such that the active blade is able to reach and maintain a specific temperature, for example, by having intermittent bursts of energy supplied to the active blade or by controlling the power or energy delivered to the active blade whenever the temperature of the active blade drops below a certain threshold level.

In one embodiment, it is envisioned that these temperature sensing MEMS devices "M" can be thermocouples positioned directly on a probe or an instrument and electrically and thermally insulated from the same for the sensing and/or measuring the temperature of tissue located adjacent thereto. It is further contemplated that, due to their relatively smaller size and sensitivities, temperature sensing MEMS devices "M" can be positioned on and/or encapsulated in thermally conductive tips or elements that could be semi-rigid wires or wires made of shape memory metals for a particular application that could be extended out from the probe and into the tissue adjoining a treatment probe in order to monitor the temperature of the tissue adjoining the treatment probe.

It is further contemplated that selected MEMS devices "M" are configured and adapted to be current sensing MEMS devices for regulating and monitoring electrical current delivered to the active blade and through the tissue. It is envisioned that the flow or amount of current could be regulated to stop after delivery of a specific amount of energy or after reaching a specific current value.

In addition, it is contemplated that selected MEMS devices "M" are configured and adapted to control the energy treatment by detecting the distance between moveable elements, such as, for example, jaws having electrodes, in order to maintain the jaws at an optimal distance for one or more aspects of a given treatment application. For example, distance sensing MEMS devices "M" can be employed to use light beams emitted from laser diodes and/or guided through fiber optics in conjunction with a detecting device, such as, for example, a bicell or a photo diode positioned directly on the tip of the probe or at a remote location suitable for measuring the relative distance between portions of the jaws.

In an alternative embodiment of the present disclosure, it is envisioned that MEMS devices "M" are configured and adapted to be accelerometer MEMS devices "M", which accelerometers detect frequencies by displacement of a cantilevered or tuned element associated with MEMS devices "M". Accordingly, when the surgical instrument is an energy based surgical instrument, for example, of the cutting or coagulating type (e.g., electrosurgical instrument) which includes a jaw mechanism 522 as described above, MEMS devices "M" employing suitable sensors can be employed for measuring the acceleration and displacement of jaw members 580, 582 in relation to each other. Accordingly, accelerometer MEMS devices "M" can be positioned on individual components, such as, for example, each jaw 580, 582, to measure their relative acceleration, on the overall surgical instrument 500 or on a fixed blade which performs the coagulating and cutting functions, such as, for example, an electrosurgical pencil to measure the acceleration of the instruments a whole, or a combination thereof.

When accelerometer MEMS devices "M" are employed and suitably integrated as two or three orthogonal assemblies, they effectively constitute a two-dimensional or three-dimensional acceleration measuring device or gyroscope type device when provided with a known point of origination and appropriately configured computer system. In this embodiment, MEMS devices "M" can be advantageously employed as a passive system for tracking the distance between the jaws, position of the instrument relative to the target tissue portion and duration of treatment.

A further application for MEMS devices "M" in surgical instruments such as electrosurgical cutting or coagulating devices includes torque sensing. It is contemplated that selected torque sensing MEMS devices "M" can be properly positioned on each jaw member 580, 582, on jaw mechanism 522 or on a combination of both. Torque sensing MEMS devices "M" can be configured and adapted to employ strain sensors or optical measuring systems, for example. It is envisioned that, torque sensing MEMS devices "M" can be configured to detect the deflection at different points along the element or handle of the instrument relative to one another. Accordingly, the deflection of portions of the surgical instrument, at predetermined points and angles of application of torque sensing MEMS devices "M", could be equated to an applied force or torque. Strain sensors or fiber optic or integrated waveguide structure in conjunction with a detection system could be used to detect, measure and control the degree of force applied to or exerted by components by monitoring the relative changes in distance or deflection of portions of the instrument.

Preferably, as seen in FIG. 6, MEMS devices "M" are electrically coupled to a control box 562 via wire leads 560 extending from housing 512. It is envisioned that wire leads 560 travel through housing 512 and shaft 518 to MEMS devices "M". In a preferred embodiment, MEMS devices "M" and control 562 box are electrically coupled to a feedback circuit (not shown). The feedback circuit would continually monitor and transmit signals and parameters between MEMS devices "M" and control box 562.

MEMS devices "M", such as those described above, may also be employed individually or in combination with traditional sensor systems, such as, for example, loss detection circuitry between elements of the instrument, and can be suitably configured to provide feedback to an electronic control system (e.g., computer, microprocessor, programmable logic controller or combination thereof) for tracking each reported feedback parameter relative to predefined criteria for the automatic adjustment and control of the energy delivered by the instrument in order to, e.g., measure, determine, verify and/or control the effectiveness of the treatment and proper performance of the surgical instrument. The control system would preferably also be configured with logic to weight the inputs of each parameter sensed by a MEMS device "M" and accommodate the selective manual operation of any parameter. Thus, parameters of MEMS devices "M" may be integrated into a single computerized display system or separately monitored, for example, by the display system or by simple audible, visual or tactile warning systems. The control system could be integrated at least partially into the instrument or a separate system connected to the instrument.

By way of example only, in accordance with the present disclosure, it is envisioned that the MEMS devices "M" can include pressure measuring devices (i.e., capacitive, piezoresistive, piezoelectric, resonant and/or optical fiber interferometric, etc.), strain measuring devices (i.e., piezoresistive, piezoelectric and/or frequency modulation, etc.), displacement measuring devices (i.e., capacitive, magnetic and/or optical fiber interferometric), optical (i.e., fluorescence, absorption and/or optical fiber interferometric), biosensors (for measuring, i.e., glucose, neural probes, tactile, pH, blood gases) and/or immunosensors, temperature sensors, torque sensors, accelerometers, flow sensors and electrochemical and/or electromagnetic sensors, and combinations of the above.

In accordance with the principles of the present disclosure, as seen in FIGS. 7-12, it is envisioned that the above described surgical instruments, together with their respective incorporated MEMS devices "M" can be employed with or interface directly with a robotic surgical system 600. An exemplary robotic surgical system is disclosed in commonly assigned U.S. Pat. No. 6,231,565 to Tovey et al., the entire contents of which is incorporated herein by reference.

Generally, robotic surgical systems include surgical instrument or systems, either powered locally or remotely, having electronic control systems localized in a console or distributed within or throughout the surgical instrument or system. The surgical instrument systems can be powered and controlled separately from the robotic system or, in the alternative, the power and control systems can be integrated or interfaced with the robotic surgical system.

Figure 7:
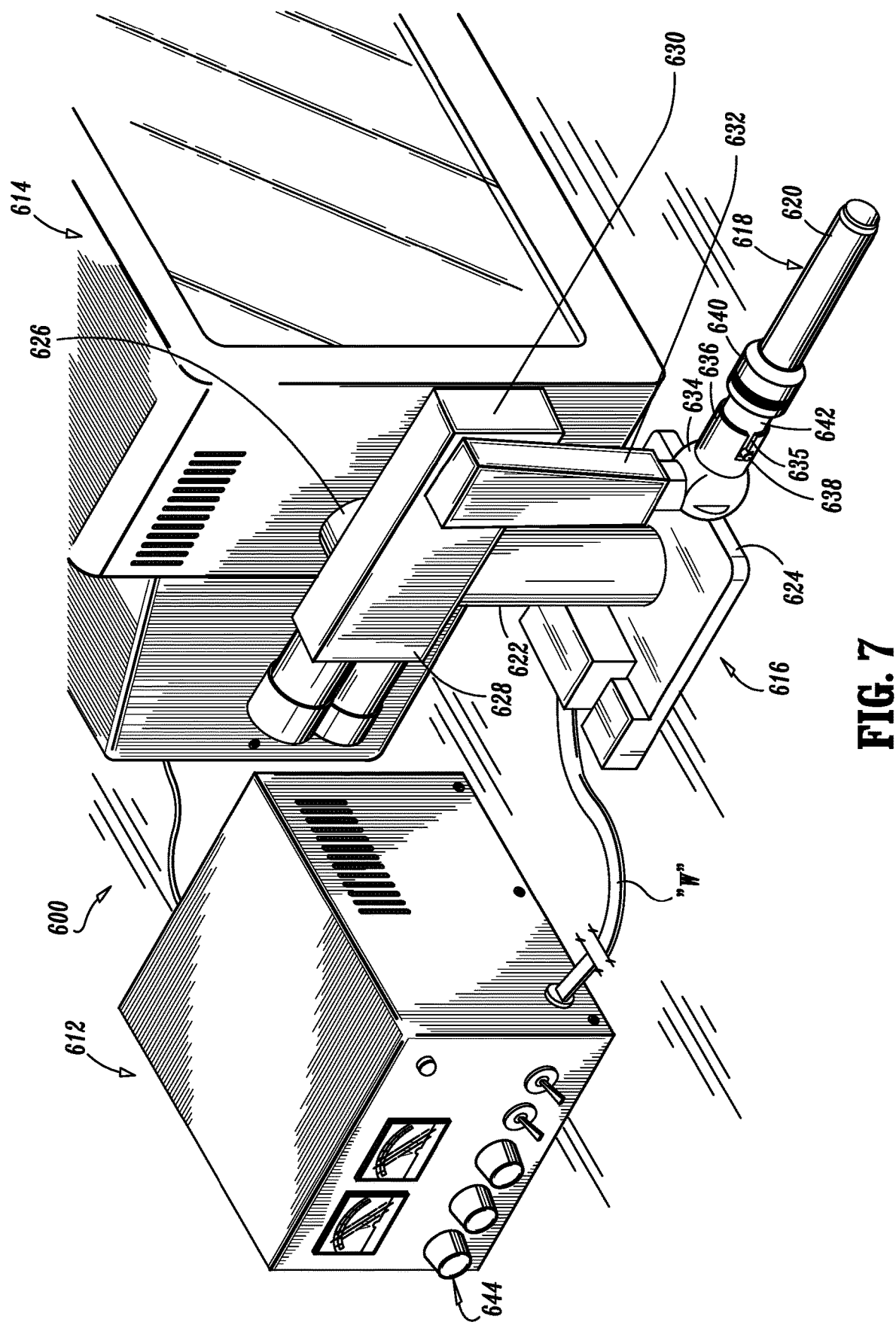
FIG. 7 is a perspective view of a robotic system that employs micro-electromechanical system devices in accordance with the present disclosure.

In particular, as seen in FIG. 7, robotic surgical system 600 includes an actuation assembly 612, a monitor 614, a robot 616 and a loading unit 618 releasably attached to robot 616 and having at least one surgical instrument 620 for performing at least one surgical task operatively connected thereto. Robot 616 includes a trunk 622 extending from a base 624, a shoulder 626 connecting trunk 622 to an upper arm 628, an elbow 630 connecting upper arm 628 to a lower arm 632, and a wrist 634 attached to lower arm 632 from which extends a mounting flange 636. Preferably, mounting flange 636 is capable of moving in six degrees of freedom.

As used herein, "loading unit" is understood to include disposable loading units (e.g., DLU's) and single use loading units (e.g., SULU's). SULU's include removable cartridge units, e.g., for open gastrointestinal anastomosis and transverse anastomosis staplers and include removable units, e.g., those having a shaft 316, a cartridge assembly 318 and an anvil 317 (see, e.g., FIG. 3 hereof). These latter removable units, which can be modified, are sometimes referred to as DLU's (e.g., see 618 in FIGS. 7 and 718 in FIG. 9).

Disposable loading unit 618 further includes a head portion 640 for housing an electro-mechanical assembly 619 (see FIG. 8) therein for operating surgical instrument 620 and an attachment platform 642 for releasably attaching disposable loading unit 618 to robot 616 via mounting flange 636. Mounting flange 636 preferably includes two slots 635 which inter-engage with protrusions 638 of platform 642 to connect to mounting flange 636 with disposable loading unit 618. It is further contemplated that an electrical connection 633 (see FIG. 8) be provided between slots 635 and protrusions 638 in order to provide power to electro-mechanical assembly 619.

Disposable loading unit 618, which could be a surgical instrument as contemplated herein, can be removed from mounting flange 636 and be replaced with another such disposable loading unit, or surgical instrument, for performing a different surgical procedure. By way of example only and in no way to be considered as limiting, potential surgical instruments or systems which can interface with robotic system 600 include various hand instruments, e.g., graspers, retractors, specimen retrieval instruments, endoscopic and laparoscopic instruments, electrosurgical instruments, stapling or fastener applying instruments, coring instruments, cutting instruments, hole-punching instruments, suturing instruments and/or any combination thereof. It is envisioned that each of these instruments be provided with at least one, preferably a plurality of MEMS devices "M" as described above, for providing feedback to the user. It is further contemplated that MEMS devices "M" can provide feedback directly to robotic system 600 in order for robotic system 600 to respond, e.g., adapt in response to the feedback and/or provide notification to the user of robotic system 600. It is further envisioned that a plurality of sensors can be incorporated into, e.g., provided on an energy based surgical instrument, which energy based surgical instrument can also be interfaced with robotic system 600. Accordingly, the energy provided to the energy based surgical instrument can be delivered and controlled directly by robotic system 600 for improved user interfaces and better system integration.

In operation, the user (e.g., surgeon, nurse, technician, etc.) controls actuation assembly 612 to control the movement and operation of robot 616 and disposable loading unit 618. Depending on the amount of rotation of knobs 644 on actuation assembly 612, actuation assembly 612 transmits electrical signals to robot 616 to electro-mechanically operate the moveable parts of robot 616, such as to rotate robot 616 about vertical trunk 622 or to advance mounting flange 636. Actuation assembly 612 may include a processor therein for storing operational commands and for transmitting digital signals to electro-mechanical assembly 619. Actuation assembly 612 can also transmit electrical signals to mounting flange 636 in the form of electrical signals, for example, for positioning and operating loading unit 618.

Actuation assembly 612 preferably is adapted to transmit electrical signals to an electro-mechanical assembly 619 housed within head portion 640 of loading unit 618 for actuating electro-mechanical assembly 619 which in turn actuates surgical instrument 620. Electro-mechanical assembly 619 includes mechanisms for moving and operating surgical tool instrument 620, such as, for example, servo motors for harmonically oscillating a scalpel or a cutting instrument, or rods for pivotally moving a suturing needle positioned on an axis of a longitudinal casing of a suturing instrument.

Figure 8:
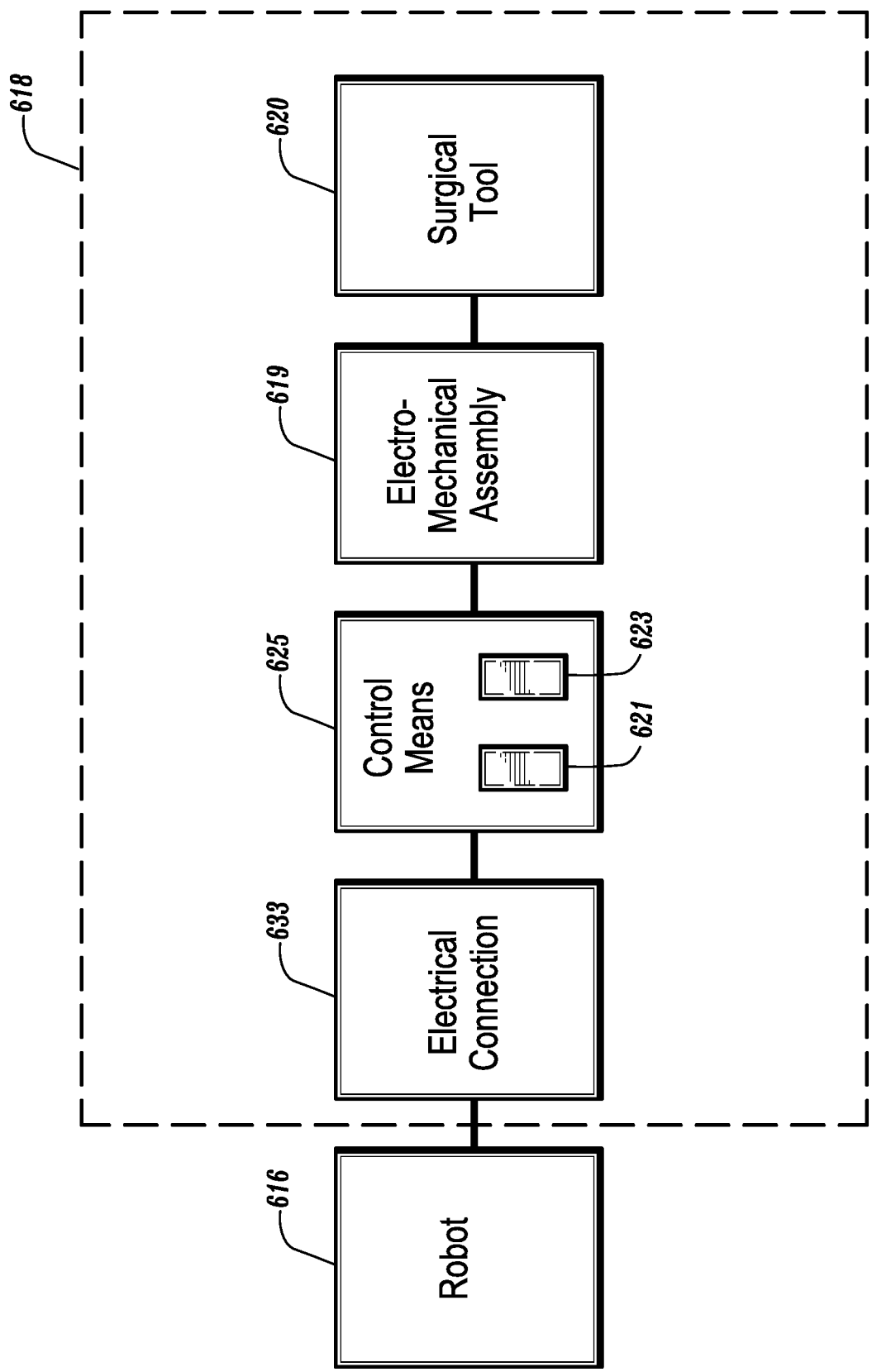
FIG. 8 is a block diagram illustrating the components of a disposable loading unit in accordance with the present disclosure.

As seen in FIG. 8, disposable loading unit 618 may further include integrated circuitry for receiving digital signals from actuation assembly 612, such as, for example, a receiver 621 and a processor 623. Receiver 621 and processor 623 are included within control means 625 electrically connected to electro-mechanical assembly 619.

Figure 9:
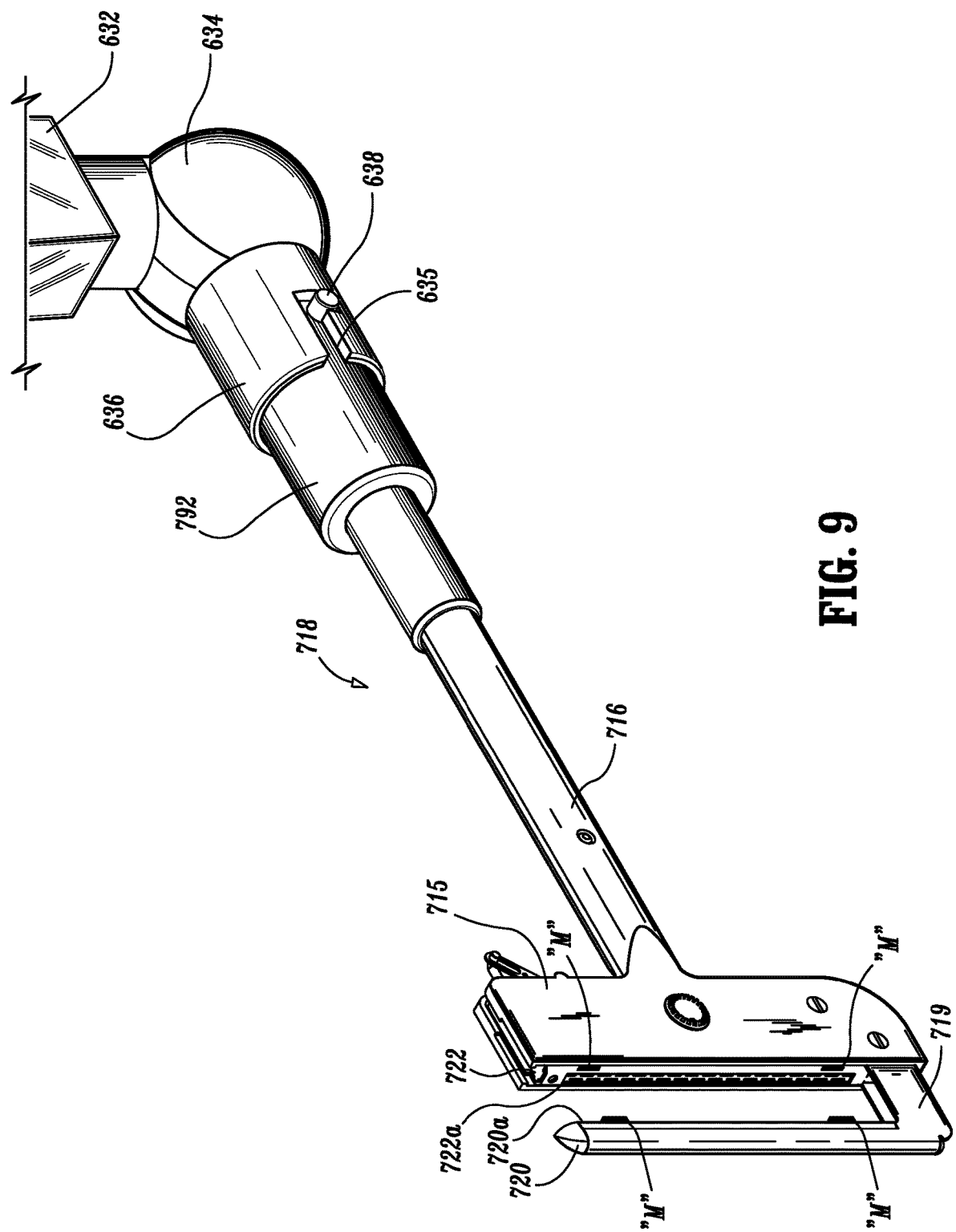
FIG. 9 is a perspective view, with portions broken away, of a robotic system coupled to a loading unit, including an end effector for applying surgical staples.

By way of example only, as shown in FIG. 9, a disposable loading unit 718, hereinafter sometimes referred to as loading unit 718, including an end effector of a surgical stapler, similar to the end effector of surgical stapler 100 described above, is operatively connected to robot 616 (see FIG. 7) such that an array of surgical fasteners (e.g., staples) can be applied to body tissue. In particular, loading unit 718 includes a distally extending body portion 716, a transverse body portion 715, and support frame 719 operatively received in a distal end of transverse body portion 715. Loading unit 718 further includes an anvil 720 and a staple cartridge assembly 722 operatively received within transverse body portion 715. Each of anvil 720 and staple cartridge assembly 722 include juxtaposed tissue contacting surfaces 720a, 722a, respectively.

It is envisioned that loading unit 718 includes an actuator incorporated within a head portion 792 to perform fast closure and incremental advancement of staple cartridge assembly 722 with respect to anvil 720. As described above, relative to surgical stapler 100, MEMS devices "M" can be provided on anvil 720 and staple cartridge assembly 722 to provide feedback information to robot 616.

Examples of direct information that can be fed back to robot 616 from MEMS devices "M" of loading unit 718 or other MEMS devices include, for example, whether staples have been fired or, in the case of an electrosurgical instrument, the amount of energy delivered. MEMS device "M" can also be used to make indirect measurements of performance, such as, for example, detecting the status of staple firing by measuring the position of the assembly member responsible for pushing the staples out of the cartridge. Alternatively, MEMS devices "M" can measure an associated member, such as a displacement of a drive rod or a rotation of a screw rod to determine whether the staples have been fired or not. In either instance, robotic system 600 can accept the information from loading unit 718 and respond accordingly, for example, by either altering performance, making adjustments, notifying the user, modifying or stopping operation or any combination thereof.

Reference is made to commonly assigned U.S. Pat. No. 5,964,394 to Robertson, the entire content of which is incorporated herein by reference, for a more detailed explanation of the operation and internal working of the components of the end effector of the surgical stapler operatively coupled to the distal end of loading unit 718.

Figure 10:
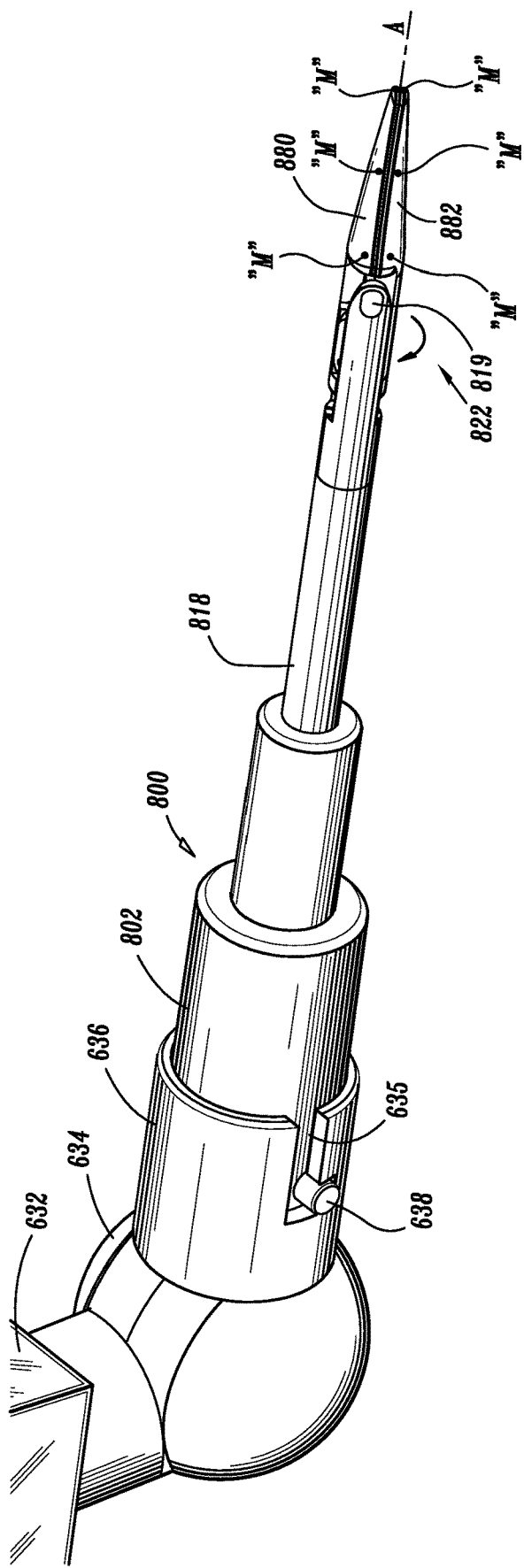
FIG. 10 is a perspective view, with portions broken away, of a robotic system coupled to a loading unit, including an end effector for applying electrosurgical energy.

As seen in FIG. 10, a loading unit including a distal end portion capable of performing an electrosurgical function, similar to surgical instrument 500 above, is shown generally as 800. In particular, loading unit 800 includes a head portion 802 configured and adapted to be removably coupled to mounting flange 636 of robot 616, an elongate shaft 818 extending distally from head portion 802, and a jaw mechanism 822 operatively coupled to a distal end of shaft 818.

Jaw mechanism 822 includes a pair of jaw members 880, 882 which are pivotable about pin 819 in order to provide the opening and closing of jaw mechanism 822. Jaw members 880, 882 are preferably configured and adapted to perform an electrosurgical function, such as, for example, coagulation, cauterization and the like.

Loading unit 800 is preferably further provided with MEMS devices "M" placed near a proximal end, a distal end, approximately mid-way and/or all along the length of each jaw member 880, 882 in order to provide feed back information to robot 616. Accordingly, in the case of loading unit 800, MEMS devices "M" can feed back, to robot 616 and actuation assembly 612, information regarding, for example, the amount of energy delivered, the clamping force being applied by jaw members 880, 882, the temperature at the target surgical site and the like.

Figure 11:
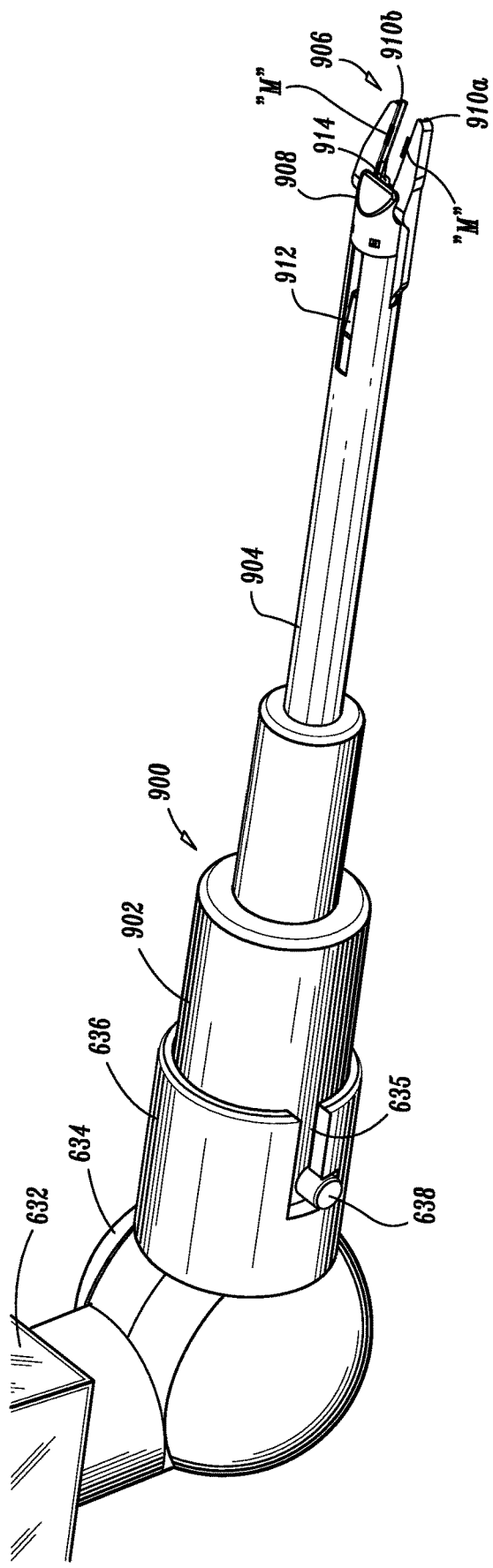
FIG. 11 is a perspective view, with portions broken away, of a robotic system coupled to a loading unit, including an end effector for applying vessel clips.

Turning now to FIG. 11, a loading unit including a vessel clip applying end effector, for applying surgical clips to body tissue, for example, for occluding vessels, is shown generally as 900. Loading unit 900 includes a head portion 902, a body portion 904 extending distally from head portion 902, and a plurality of surgical clips (not shown) disposed within body portion 904. A jaw assembly 906 is mounted adjacent a distal end portion 908 of body portion 904. Jaw assembly 906 includes a first and a second jaw portion 910a, 910b, respectively, which are movable between a spaced-apart and approximated position relative to one another.

A clip pusher (not shown) is provided within body portion 904 to individually distally advance a distal-most surgical clip to jaw assembly 906 while first and second jaw portions 910a, 910b are in the spaced-apart position. An actuator 912, disposed within body portion 904, is longitudinally movable in response to actuation of electro-mechanical assembly 619 provided within head portion 902. A jaw closure member 914 is positioned adjacent first and second jaw portions 910a, 910b to move jaw portions 910a, 910b to the approximated position. Actuator 912 and jaw closure member 914 define an interlock therebetween to produce simultaneous movement of actuator 912 and jaw closure member 914 when actuator 912 is positioned adjacent the distal end portion of body portion 904.

It is envisioned that loading unit 900 preferably includes at least one MEMS device "M" operatively connected to each of the first and second jaw portions 910a, 910b to provide feedback information to robot 616.

Reference is made to commonly assigned U.S. Pat. No. 6,059,799 to Aranyi et al., the entire content of which is incorporated herein by reference, for a more detailed explanation of the operation and internal working of the components of the vessel clip applying end effector of loading unit 900.

Figure 12:
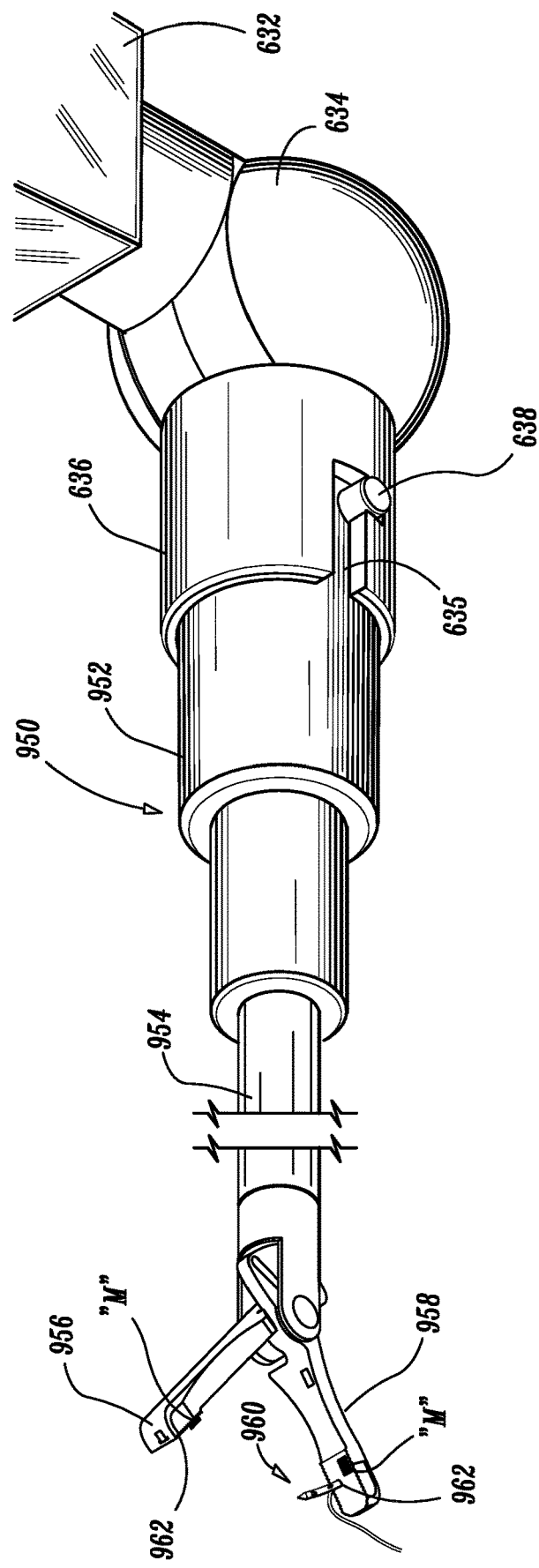
FIG. 12 is a perspective view, with portions broken away, of a robotic system coupled to a loading unit, including an end effector for applying a vascular suture.

Turning now to FIG. 12, a loading unit including a vascular suture applying end effector, for suturing vascular tissue sections together, is shown generally as 950. Loading unit 950 includes a head portion 952 and a body portion 954 extended distally therefrom. A pair of needle receiving jaws 956, 958 are pivotally mounted at a distal end of body portion 954 and are configured to repeatedly pass a surgical needle 960 and associated length of suture material therebetween. Loading unit 950 further includes needle holding structure (not shown) mounted within jaws 956 for reciprocal movement into and out of needle holding recesses 962 formed in jaws 956, 958. During an anastomosis procedure, loading unit 950 will advantageously respond to movement commands transmitted from the actuation assembly to apply fasteners to tissue.

It is envisioned that loading unit 950 preferably includes at least one MEMS device "M" operatively connected to each of the pair of needle receiving jaws 956, 958 to provide feedback information to robot 616. It is contemplated that MEMS device "M" can, for example, provide information relating to the position of jaws 956, 958, whether and in which jaw needle 960 is disposed, and the force being exerted on needle 960.

Reference is made to commonly assigned U.S. Pat. No. 5,478,344 to Stone et al., the entire content of which is incorporated herein by reference, for a more detailed explanation of the operation and internal working of the components of the vascular suture applying end effector of loading unit 950.

An advantage of using MEMS devices in conjunction with robotic systems, similar to those described above, is that conditions and forces sensed by the MEMS devices provided on the end effectors of the loading units can be fed back system to the robotic systems or transmitted to a user interface.

Current robotic systems allow little to no tactile information to reach or be transmitted from the patient back to the hands of the user (i.e., the surgeon). Accordingly, by using MEMS devices, in accordance with the present disclosure, in combination with a feedback and control system, conditions and forces experienced by the distal end of the end effectors due to the interaction of the end effector with the tissue of the patient can be "felt" and/or monitored by the surgeon, thus greatly improving the surgeon's information and, in turn, ability to perform surgical procedures.

In accordance with the present disclosure, it is contemplated to have feedback of information, data, signals, conditions and forces, initiated by pressure and/or other parameters indicative of the surgical task being performed by the end effector of the disposable loading unit and measured and/or sensed by MEMS devices provided on the loading unit, and to transmit this feedback to a control system. This feedback control system allows the robotic system to be programmed, before the surgical task is performed, with guidance, pressure, and other parameters which can be continuously monitored to control the operation and movement of the loading unit and of the associated end effector.

Although the illustrative embodiments of the present disclosure have been described herein, it is understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A robotic system for performing surgical tasks, the robotic system comprising:
    a robotic arm;
    an actuation assembly operatively associated with the robotic arm for controlling operation and movement of the robotic arm, the actuation assembly including a processor for storing operational commands;
    a loading unit releasably connected to the robotic arm, the loading unit being selected from the group consisting of a surgical stapler, an electro surgical instrument, a clip applier, and a suture applying instrument, and including:
        a head portion for housing an electro-mechanical assembly configured to receive signals from the processor of the actuation assembly; and
        at least one micro-electromechanical system (MEMS) device including:
            an energy producing device; and
            a sensor configured to sense energy produced by the energy producing device, wherein the at least one MEMS device is configured to determine a distance between movable components of the loading unit by timing a duration between initial energy sensing by the sensor and activation of the energy producing device.

2. The robotic system of claim 1, wherein the movable components are a pair of jaw members, the MEMS device being positioned on at least one jaw member of the pair of jaw members.

3. The robotic system of claim 2, wherein the at least one MEMS device is configured to determine a distance between the pair of jaw members.

4. The robotic system of claim 2, wherein the at least one MEMS device is operatively connected to a tissue contacting surface of each of the pair of jaw members.

5. The robotic system of claim 2, wherein the energy producing device is attached to a first jaw member of the pair of jaw members of the loading unit, and the sensor is attached to a second jaw member of the pair of jaw members.

6. The robotic system of claim 1, wherein the loading unit is connected to the robotic arm via a bayonet-type connection.

7. The robotic system of claim 1, further comprising a controller including a receiver for receiving electrical signals transmitted from the actuation assembly and for controlling operation and movement of the loading unit.

8. The robotic system of claim 1, further comprising a feedback control system configured to allow the robotic system to be programmed, before a surgical task is performed, to continuously monitor, in real-time, a plurality of parameters and operations associated with movement of the loading unit.

9. The robotic system of claim 1, wherein the at least one MEMS device includes a wireless transmitter.

10. The robotic system of claim 1, further comprising a frame, wherein the robotic arm is connected to the frame and movable in six degrees of freedom relative to the frame.

* * * * *